(12) United States Patent
Aguiar

(10) Patent No.: US 10,195,260 B2
(45) Date of Patent: Feb. 5, 2019

(54) ANTIGEN FOR USE IN MALARIA

(71) Applicant: CAMRIS International, Inc., Bethesda, MD (US)

(72) Inventor: Joao Carlos Aguiar, Potomac, MD (US)

(73) Assignee: CAMRIS International, Inc., Bethesda, MD (US)

( * ) Notice: Subject to any disclaimer, the term of this patent is extended or adjusted under 35 U.S.C. 154(b) by 0 days.

(21) Appl. No.: 15/431,609

(22) Filed: Feb. 13, 2017

(65) Prior Publication Data

US 2017/0232091 A1 Aug. 17, 2017

Related U.S. Application Data

(60) Provisional application No. 62/296,464, filed on Feb. 17, 2016.

(51) Int. Cl.
*A61K 39/015* (2006.01)
*A61K 39/00* (2006.01)

(52) U.S. Cl.
CPC .... *A61K 39/015* (2013.01); *A61K 2039/5256* (2013.01); *A61K 2039/545* (2013.01); *A61K 2039/70* (2013.01); *C12N 2710/10043* (2013.01); *Y02A 50/412* (2018.01)

(58) Field of Classification Search
None
See application file for complete search history.

(56) References Cited

U.S. PATENT DOCUMENTS

2015/0366958 A1 12/2015 Chen et al.

FOREIGN PATENT DOCUMENTS

WO WO 2015/052543 A2 4/2015
WO WO 2017/142843 A1 8/2017

OTHER PUBLICATIONS

Ellis (Vaccines, W.B. Saunders Company, Chapter 29, 1988, pp. 568-574).*
Boslego et al (Vaccines and Immunotherapy, 1991, Chapter 17).*
Skolnick et al., the art is unpredictable. Skolnick et al. (Trends in Biotechnology 18: 34-39, 2000).*
Bowman et al., "The complete nucleotide sequence of chromosome 3 of *Plasmodium falciparum*," Nature 400:532-8, Nature Publishing Group, England (1999).
Carlton, et al., "Genome sequence and comparative analysis of the model rodent malaria parasite *Plasmodium yoelii yoelii*," Nature 419:512-9, Nature Publishing Group, England (2002).
Carlton, et al., "Comparative genomics of the neglected human malaria parasite *Plasmodium vivax*," Nature 455:757-63, Nature Publishing Group, England (2008).
GenPept, "hypothetical protein, conserved [Plasmodium vivax]," Accession No. XP_001613586.1, accessed at https://www.ncbi.nlm.nih.gov/protein/XP001613586 on May 17, 2018.
Gardner, et al., "Genome sequence of the human malaria parasite *Plasmodium falciparum*," Nature 419:498-511, Nature Publishing Group, England (2002).
Hall, N., et al., "Sequence of Plasmodium falciparum chromosomes 1, 3-9 and 13," Nature 419:528 (Abstract No. 6906), Nature Publishing Group, England (2002).
International Search Report for International Application No. PCT/US2017/017722, European Patent Office, Netherlands, dated Jul. 3, 2017, 6 pages.
Lasonder, E., et al., "Proteomic profiling of *Plasmodium* sporozoite maturation identifies new proteins essential for parasite development and infectivity," PLOS Pathogens 4(10):e1000195, Public Library of Science, United States (2008).
Mobegi, V.A., et al., "Genome-wide analysis of selection on the malaria parasite *Plasmodium falciparum* in West African populations of differing infection endemicity," Mol Biol Evol. 31(6):1490-9, Oxford University Press, England (2014).
Silberhorn, E., et al., "*Plasmodium falciparum* Nucleosomes exhibit reduced stability and lost sequence dependent nucleosome positioning," PLOS Pathogens 12(12): e1006080, Public Library of Science, United States (2016).

* cited by examiner

*Primary Examiner* — Robert A Zeman
(74) *Attorney, Agent, or Firm* — Sterne, Kessler, Goldstein & Fox P.L.L.C.

(57) ABSTRACT

The present invention provides polypeptides useful as antigens expressed at the pre-erythrocytic stage of the malaria parasite. The antigens can be utilized to induce an immune response and sterile protection against malaria in a mammal by administering the antigens in vaccine formulations or expressing the antigens in DNA or other recombinant protein expression systems delivered as a vaccine formulation.

18 Claims, 16 Drawing Sheets

Specification includes a Sequence Listing.

E140 Antigen Homology Amongst *Plasmodium spp*

| | Pf E140 | Pv E140 | Py E140 | Pb E140 | Pc E140 | Pk E140 | Pr E140 | Pg E140 |
|---|---|---|---|---|---|---|---|---|
| Pf E140 | — | | | | | | | |
| Pv E140 | 43% | — | | | | | | |
| Py E140 | 35% | 37% | — | | | | | |
| Pb E140 | 36% | 36% | 86% | — | | | | |
| Pc E140 | 37% | 37% | 67% | 67% | — | | | |
| Pk E140 | 43% | 78% | 36% | 36% | 34% | — | | |
| Pr E140 | 92% | 43% | 35% | 35% | 37% | 43% | — | |
| Pg E140 | 81% | 44% | 34% | 35% | 35% | 43% | 82% | — |

Pf - *P. falciparum*
Pv - *P. vivax*
Pc - *P. chabaudi*
Py - *P. yoelii*
Pb - *P. berghei*
Pk - *P. knowlesi*
Pr - *P. reichenowi*
Pg - *P. gaboni*

FIG. 7

E140 Antigen is Highly Conserved Amongst *P. falciparum* Strains

| | 3D7 | UGT5.1 | 7G8 | Mali | UGPA | HB3 | Santa Lucia | IGH-CR14 | FCH/4 | NF135/5.C10 | Tanzania | FVO |
|---|---|---|---|---|---|---|---|---|---|---|---|---|
| 3D7* | --- | | | | | | | | | | | |
| UGT5.1** | 98% | --- | | | | | | | | | | |
| 7G8 (Brazil) | 97% | 97% | --- | | | | | | | | | |
| Mali PS096 | 97% | 99% | 96% | --- | | | | | | | | |
| UGPA*** | 97% | 97% | 97% | 98% | --- | | | | | | | |
| HB3 (Honduras) | 97% | 97% | 98% | 98% | 98% | --- | | | | | | |
| Santa Lucia**** | 97% | 97% | 97% | 98% | 98% | 98% | --- | | | | | |
| IGH-CR14$ | 97% | 96% | 96% | 97% | 97% | 97% | 97% | --- | | | | |
| FCH/4⌘ | 97% | 98% | 97% | 98% | 97% | 98% | 99% | 96% | --- | | | |
| NF135/5✧ | 97% | 98% | 97% | 99% | 98% | 98% | 99% | 96% | 99% | --- | | |
| Tanzania | 93% | 93% | 94% | 92% | 93% | 93% | 93% | 92% | 93% | 93% | --- | |
| FVO (Vietnam) | 96% | 96% | 95% | 97% | 96% | 96% | 98% | 95% | 98% | 98% | 95% | --- |
| Dd2 (Indochina) | 97% | 96% | 97% | 94% | 96% | 96% | 96% | 94% | 96% | 96% | 98% | 96% |

\* - The Netherland  
\** - Uganda  
\*** - Uganda/palo Alto  
\**** - El Salvador  
$ - India (Rourkela, Orissa)  
⌘ - The Philippines  
✧ - Cambodia (CHMI)

FIG. 8

P. falciparum PFA0205w (PfE140) is Immunogenic in Mice.

| Vaccines | CD1 IFA Titer | | BALB/c IFA Titer | |
|---|---|---|---|---|
| | Sporozoite | Blood Stage | Sporozoite | Blood Stage |
| PFA0205w DNA/Ad5 | Negative | Negative | 250 | Negative |
| PFA0205wDNA/Ad5 | 20 | Negative | 250 | Negative |
| PFA0205w Ad5/GST Protein | 1000 | 500 | 1000 | 250 |
| PFA0205w Ad5/GST Protein | 2000 | 4000 | 500 | Negative |
| PFA0205w DNA x3 | Negative | Negative | 250 | Negative |
| PFA0205w DNA x3 | Negative | Negative | 250 | Neat |
| PFA0205w His Protein | Negative | Negative | Neat | Negative |
| PFA0205w His Protein | Negative | Negative | Neat | Negative |
| PFA0205w GST Protein | Negative | 20 | 250 | 20 |
| PFA0205w GST Protein | Negative | 20 | Negative | 250 |

ANTIGEN FOR USE IN MALARIA

CROSS-REFERENCE TO RELATED APPLICATIONS

This application claims priority under 35 U.S.C. § 119(e) from U.S. Provisional Patent Application Ser. No. 62/296,464 filed Feb. 17, 2016, the entirety of which is hereby incorporated by reference herein.

BACKGROUND

Despite years of effort, a licensed malaria vaccine is not available. One of the obstacles facing the development of a malaria vaccine is the extensive heterogeneity of many of the malaria vaccine antigens. Potential vaccine antigens that have been evaluated in people thus far have not elicited a protective immune response.

Malaria kills approximately 863,000 people every year. Although a variety of anti-malarial drugs exist, the cost of these drugs can be prohibitive in the relatively poor areas of the world where malaria is endemic. The widespread use of the most commonly employed drugs has also resulted in the expansion of drug-resistant parasites, rendering many of these drugs ineffective. In the absence of inexpensive, highly potent drugs, vaccination represents the most cost-effective way of supplementing traditional malaria interventions.

A successful malaria vaccine will need to protect people against a large population of antigenically diverse malaria parasites. A vaccine based on a single isolate of a single antigen may not be able to elicit an immune response that is broad enough to protect individuals against this heterogeneous population. One way to potentially enhance the efficacy of antigen-based vaccines, or any other subunit malaria vaccine, would be to incorporate additional malaria antigens into the vaccine, thereby broadening the immune response elicited by the vaccine.

Malaria vaccine development efforts have focused almost exclusively on a handful of well-characterized *Plasmodium falciparum* antigens. Despite dedicated work by many researchers on different continents spanning more than half a century, a successful malaria vaccine remains elusive. Sequencing of the *P. falciparum* genome has revealed more than five thousand genes, but has given no indication which of these five thousand genes will be useful, or how to identify potential vaccine targets.

Malaria is caused by mosquito-borne hematoprotozoan parasites belonging to the genus *Plasmodium*. Four species of *Plasmodium* protozoa (*P. falciparum, P. vivax, P. ovale* and *P. malariae*) are responsible for the disease in humans. Others cause disease in animals, such as *P. yoelii* and *P. berghei*. *P. falciparum* accounts for the majority of infections and deaths in humans. Malaria parasites have a life cycle consisting of four separate stages. Each one of these stages is able to induce specific immune responses directed against the parasite and the correspondingly occurring stage-specific antigens, yet naturally induced malaria does not protect against reinfection.

Malaria parasites are transmitted to mammals by several species of female *Anopheles* mosquitoes. Infected mosquitoes deposit the sporozoite form of the malaria parasite into the mammalian skin during a blood meal, which subsequently invades the bloodstream. Sporozoites remain for a few minutes in the circulation before invading hepatocytes. At this stage, the parasite is located in the extra-cellular environment and is exposed to antibody attack, mainly directed to the circumsporozoite (CS) protein, a major component of the sporozoite surface. Once sporozoites invade hepatocytes, the parasite differentiates, replicates and develops into a schizont. During this stage, the invading parasite will undergo asexual multiplication, producing up to 20,000 daughter merozoites per infected hepatocyte cell. During this intracellular stage of the parasite, the host immune response includes T lymphocytes, especially $CD8^+$ T lymphocytes. After 10-14 days of liver infection, thousands of newly formed merozoites are released into the bloodstream and invade red blood cells (RBCs), becoming targets of antibody-mediated immune response and T-cell secreted cytokines. After invading the erythrocytes, the merozoites undergo several stages of replication, transforming into trophozoites, and schizonts, which rupture to produce a new generation of merozoites that subsequently infect new RBCs. This phase (erythrocytic) of the parasite stimulates a strong humoral response that can block merozoite invasion of RBCs and usually confers protection against pathology associated with this phase. The erythrocytic stage is associated with overt clinical disease. A smaller number of trophozoites may develop into male or female gametocytes, which are the parasite's sexual stage. When susceptible mosquitoes ingest gametocytes, the fertilization of these gametes leads to zygote formation and subsequent transformation into ookinetes, then into oocysts, and finally into sporozoites, which migrate to the salivary gland to complete the cycle.

The two major arms of the pathogen-specific immune response that occur upon entry of the parasite into the body are cellular and humoral. The one arm, the cellular response, relates to $CD8^+$ and $CD4^+$ T cells that participate in the immune response. Cytotoxic T lymphocytes (CTLs) are able to specifically kill infected cells that express pathogenic antigens on their surface. CD4+ T cells or T helper cells support the development of CTLs, produce various cytokines, and also help induce B cells to divide and produce antibodies specific for the antigens. During the humoral response, B cells specific for a particular antigen become activated, replicate, differentiate and produce antigen-specific antibodies.

Both arms of the immune response are relevant for protection against a malarial infection. When infectious sporozoites travel to the liver and enter the hepatocytes, the sporozoites become intracellular pathogens, spending little time outside the infected cells. At this stage, $CD8^+$ T cells and $CD4^+$ T cells are especially important because these T cells and their cytokine products, such as interferon-γ (IFN-γ), contribute to the killing of infected host hepatocytes. Elimination of the intracellular liver parasites in the murine malaria model is found to be dependent upon $CD8^+$ T cell responses directed against peptides expressed by liver stage parasites. Depletion of $CD8^+$ T cells abrogates protection against sporozoite challenge, and adoptive transfer of $CD8^+$ T cells to naïve animals confers protection.

When a malarial infection reaches the erythrocytic stage in which merozoites replicate in RBCs, the merozoites are also found circulating freely in the bloodstream for a brief period until they invade new erythrocytes. Because the erythrocyte does not express either Class I or II MHC molecules required for cognate interaction with T cells, it is thought that antibody responses against the parasite are most relevant at the blood stage of the parasite lifecycle. In conclusion, a possible malaria vaccine approach would be most beneficial if it would induce a strong cellular immune response as well as a strong humoral immune response to tackle the different stages in which the parasite occurs in the human body.

Current approaches to malaria vaccine development can be classified according to the different developmental stages of the parasite, as described above. Three types of possible vaccines can be distinguished. The first is pre-erythrocytic vaccines, which are directed against sporozoites and/or schizont-infected hepatocytes. Historically, this approach has been dominated by (CSP)-based strategies. Since the pre-erythrocytic phase of infection is asymptomatic, the goal of a pre-erythrocytic vaccine would be to confer sterile immunity, mediated by humoral and cellular immune response, and thereby prevent latent malaria infection. This goal has not been met by any known treatment.

The second type of vaccine approach is asexual blood stage vaccines, which are directed against either the infected RBC or the merozoite itself, are designed to minimize clinical severity or prevent infection if antibodies prevent merozoites invading erythroctyes. Attempts to create such vaccines so far have failed to sufficiently reduce morbidity and mortality or prevent the parasite from entering and/or developing in the erythrocytes. Transmission-blocking vaccines are designed to hamper the parasite development in the mosquito host. Attempts to create this type of vaccine so far have failed to reduce population-wide malaria infection rates.

The final type of vaccine approach is combination malaria vaccines that target multiple stages of the parasite life cycle. This approach attempts to develop multi-component and/or multi-stage vaccines. Attempts to create such vaccines so far have failed to effect sufficient protection. As a result of these failures, there is currently no commercially available vaccine against malaria.

Immunization of rodents, non-human primates, and humans with radiation-attenuated sporozoites (RAS) has been found to confer protection against a subsequent challenge with viable sporozoites. However, the expense and the lack of a feasible large-scale culture system for the production of irradiated sporozoites, the relative short-term efficacy, lack of cross-strain protection, and the need to be delivered intravenously have been obstacles to the development of such vaccines.

The CS protein is the only *P. falciparum* antigen demonstrated to prevent malaria infection when used as the basis of active immunization in humans against mosquito-borne infection. The protection levels for this antigen, however, are not high enough to support a viable therapy. In theory, vaccine protection levels should be above 85% in order to be a viable therapy. With protection lower than that, mutants that are more virulent may escape in endemic areas. CS antigen-based vaccines have demonstrated an efficiency of only about 50% and that protection does not last more than a year. Nevertheless, this is still the best known antigen response prior to the present disclosure.

The entire genomic sequence of *P. falciparum* has been sequenced. See Bowman et al., Nature, 400: 532-538 (1999); Gardner, et al., Nature, 419: 498-511 (2002). Another human malaria parasite, *P. vivax*, has also been sequenced. See Carlton et al., Nature, 455: 757-763 (2008). The rodent malaria parasite, *P. yoelii* has also been sequenced. See Carlton et al., Nature, 419: 512-519 (2002). Despite this, however, the development of efficacious antimalaria vaccines has been severely hampered by the inability to identify promising antigens. Sequencing of the *P. falciparum*, *P. vivax*, and *P. yoelii* genomes has resulted in the identification of 5,369, 5,433, and 5,675 genes, respectively. Knowledge of these sequences alone, however, will not likely result in new vaccine constructs. Consequently, only 0.2% of the *P. falciparum* proteome is undergoing clinical testing, and these tests have failed to induce high grade protection in volunteers.

SUMMARY

The present invention provides polypeptides useful as antigens that are expressed at both the pre- and erythrocytic stage of the malaria parasite. The antigens can be utilized to induce both cellular and humoral immune responses against malaria in a mammal by administering the antigens in vaccine formulations or expressing the antigens in DNA or other nucleic acid expression systems delivered as a vaccine formulation. In preferred embodiments, the mammal is a human.

In one preferred embodiment, the invention provides an immunogenic composition for protecting a mammal against malaria infection, the immunogenic composition comprising one or more recombinant polypeptides of SEQ ID NO. 3 or SEQ ID NO. 6, or derivatives thereof in a pharmaceutically acceptable carrier. In general, derivatives have at least 10 contiguous amino acids of and/or 85% identity with the reference sequence. The immunogenic composition can be formed from an isolated or recombinant polypeptide or a carrier virus expressing the recombinant antigen and may be paired with an acceptable adjuvant.

The antigens that are the subject of the present disclosure are identified by different nomenclatures in different contexts, as is standard in this art. For convenience, the table below identifies each antigen by its sequence, as well as the various names and shorthands used in the prior art and in the disclosure herein:

| Shorthand | PlasmoDB Identification | SEQ ID NO. |
|---|---|---|
| Py E140 | PY06306, PY17X_0210400, PYYM_0211900 | 1 (amino acid) 2 (nucleotide) |
| Pf E140 | PFA0205w, MAL1P1.31, PF3D7_0104100, XP_001350973 | 3 (amino acid) 4 (nucleotide) |
| Pv E140 | PVX_081555, PV081555, PVP01_0210600 | 6 (amino acid) 5 (nucleotide) |
| Py falstatin | PY17X_0816300, PY03424, PYYM_0816000 | |
| PyCSP | PY03168, PYYM_0405600 | |
| Py E057 | PY03396, PY17X_1006600, PYYM_1006600 | |
| Py E137 | PY05693, PY17X_1006100, PYYM_1006100 | |
| Py UIS3 | PY03011, PY17X_1402400 | |
| Pf falstatin, ICP | PFI0580C or PF3D7_0911900 | 7 (amino acid) |
| Pf CSP | PFC0210C, MAL3P2.11, PF3D7_0304600 | 8 (amino acid) |
| Pf UIS3, ETRAMP13 | PF13_0012, PF3D7_1302200 | 9 (amino acid) |

The invention may comprise a combination of two or more recombinant polypeptides in a pharmaceutically acceptable carrier, wherein one polypeptide is SEQ ID NO. 3, SEQ ID NO. 6, or derivatives thereof, and the other polypeptide is any of the *falciparum* or *vivax* orthologs of PyCSP, Py falstatin, Py UIS3, PY03396, PY05693, PY03424, and PY03011.

The present invention also includes a method of inducing an immune response against malaria in a mammal by administering an immunologically effective amount of a composition comprising one or more polypeptides encoded by SEQ ID NO. 3 or 6, or derivatives thereof. Alternatively, the method may include administering one or more priming or boosting immunizations against malaria, wherein said priming and boosting immunizations comprise an immunologically effective amount of an recombinant polypeptide as described. The method of administering the polypeptide can include use of a suitable expression vector, such as a plasmid, replicating viral vector, or nonreplicating viral vector. A suitable expression vector can be a DNA plasmid, baculovirus, rVSV, SpyVLPs, alphavirus replicon, adenovirus, poxvirus, adenoassociated virus, cytomegalovirus, canine distemper virus, yellow fever virus, retrovirus, RNA replicon, DNA replicon, alphavirus replicon particle, Venezuelan Equine Encephalitis virus, Semliki Forest Virus, or Sindbis Virus.

The polypeptides useful as antigens disclosed herein are the first *Plasmodium* pre-erythrocytic antigens that can sterilely protect 100% of subjects against an infectious *P. yoelii* sporozoite challenge. These responses are conveniently measured in mice as a proxy for their human orthologs. Malaria infection, treatment, and immunity has been studied extensively in both mice and humans, and mouse models are considered a standard indicator of malaria vaccine efficacy in human and other mammalian subjects. The PY06306 antigen disclosed herein alone protects 71% to 100% of CD1 mice against malaria and in addition induces an immune response capable of delaying the parasite onset in the blood of remaining non-protected mice. Overall, 83% (384/461) of PY06306-immunized mice were protected from malaria infection. This protection is reported for both outbred (CD1) and inbred (BABB/c) strains of mice, using a rigorous 300- and 100-sporozoite challenge, respectively, and efficacy assessment as sterile protection. The efficacy of the antigen disclosed herein, in light of the relationships among murine, primate, and human malaria immune responses disclosed herein, and standard indicators of vaccine efficacy, presents a polypeptide for inducing an immune response against malaria in a mammal.

BRIEF DESCRIPTION OF DRAWINGS

FIG. 7 shows the PY06306 (Py E140) antigen homology among *Plasmodium* spp, including Pf (human *P. falciparum*), Pv (human *P. vivax*), Pc (rodent *P. chabaudi*), Py (rodent *P. yoelii*), Pb (rodent *P. berghei*), Pk (primate *P. knowlesi*), Pr (primate *P. rhodiani*), and Pg (primate *P. gaboni*).

FIG. 8 shows the PY06306 (Pf E140) (PFA0205w or MAL1P1.31 or PF3D7_0104100) amino acid conservation among various Pf parasite strains. These parasites were collected from a variety of countries in different continents. The highest (99%) and the lowest (92%) homology are highlighted.

In FIG. 10A, groups of 14 BALB/c mice were either immunized with DNA/Adeno virus 5 encoding PY06306 (solid black line) and PyCSP (solid gray line). Sera from immunized and non-challenged mice were collected and transferred 24 and 6 hours before challenge to naïve recipient mice; PY06306 (dotted black line) and PyCSP (dotted gray line). After challenge with 300 P. yoelii sporozoites, mice were monitored for parasitaemia for 17 days. In FIG. 10B, groups of 14 CD1 mice were either immunized with DNA/Adeno virus 5 encoding PY06306 (solid black line) and PyCSP (solid gray line). Sera from immunized and non-challenged mice were collected and transferred 24 and 6 hours before challenge to naïve recipient mice; PY06306 (dotted black line) and PyCSP (dotted gray line). After challenge with 100 P. yoelii sporozoites, mice were monitored for parasitaemia for 17 days. Percentage of sterilely protected mice for each group is shown in the legend box.

FIG. 13 shows that Pf E140 (PFA0205w or MAL1P1.31 or PF3D7_0104100) is immunogenic in mice. IFA titers induced by PFA0205w vaccines. Both CD1 and BALB/c mice were immunized with PFA0205w (PfE140) vaccines reagents: DNA vaccine in VR1020-DV plasmid, Adenovirus 5, and full length recombinant protein expressed by the wheat germ system as GST and 6×His fusions. Recombinant proteins were emulsified in Montanide ISA 720 adjuvant and immunized SC as 5 µg/dose Immunofluorescence (IFA) titers were measured against both P. falciparum sporozoites and a mixture of several of blood stages.

Figure 15:
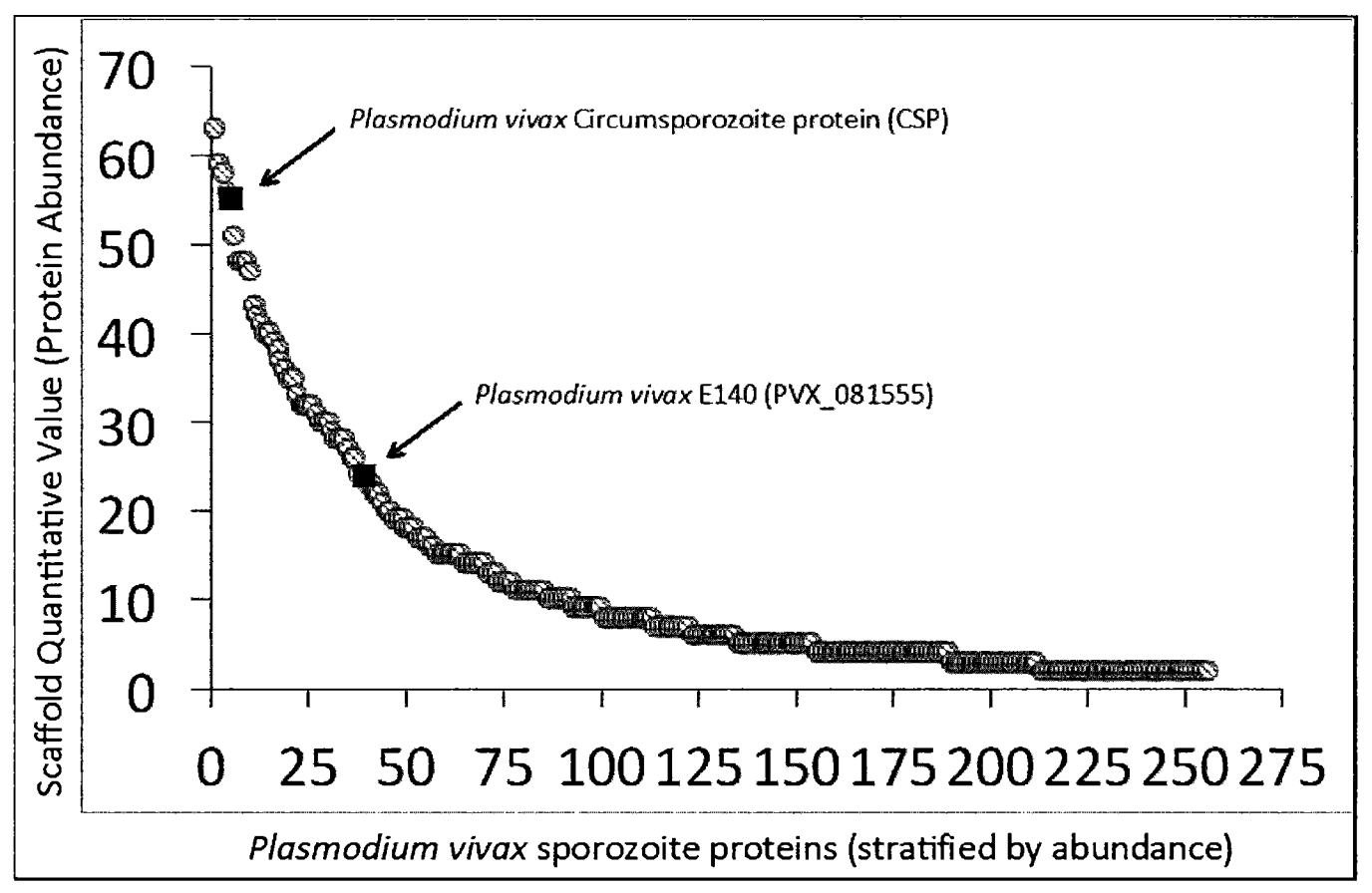

FIG. 15 shows that PVX_081555 (PvE140) is relatively abundant in P. vivax sporozoites. 256 P. vivax sporozoite proteins sequenced using multi-dimensional-protein-identification-technology (MudPIT) were graphed based on their relative abundance defined by their quantitative value. The positions of P. vivax circumsporozoite protein and P. vivax E140 (PVX_081555) are indicated in the graph with a black arrow.

DETAILED DESCRIPTION

Figure 1:
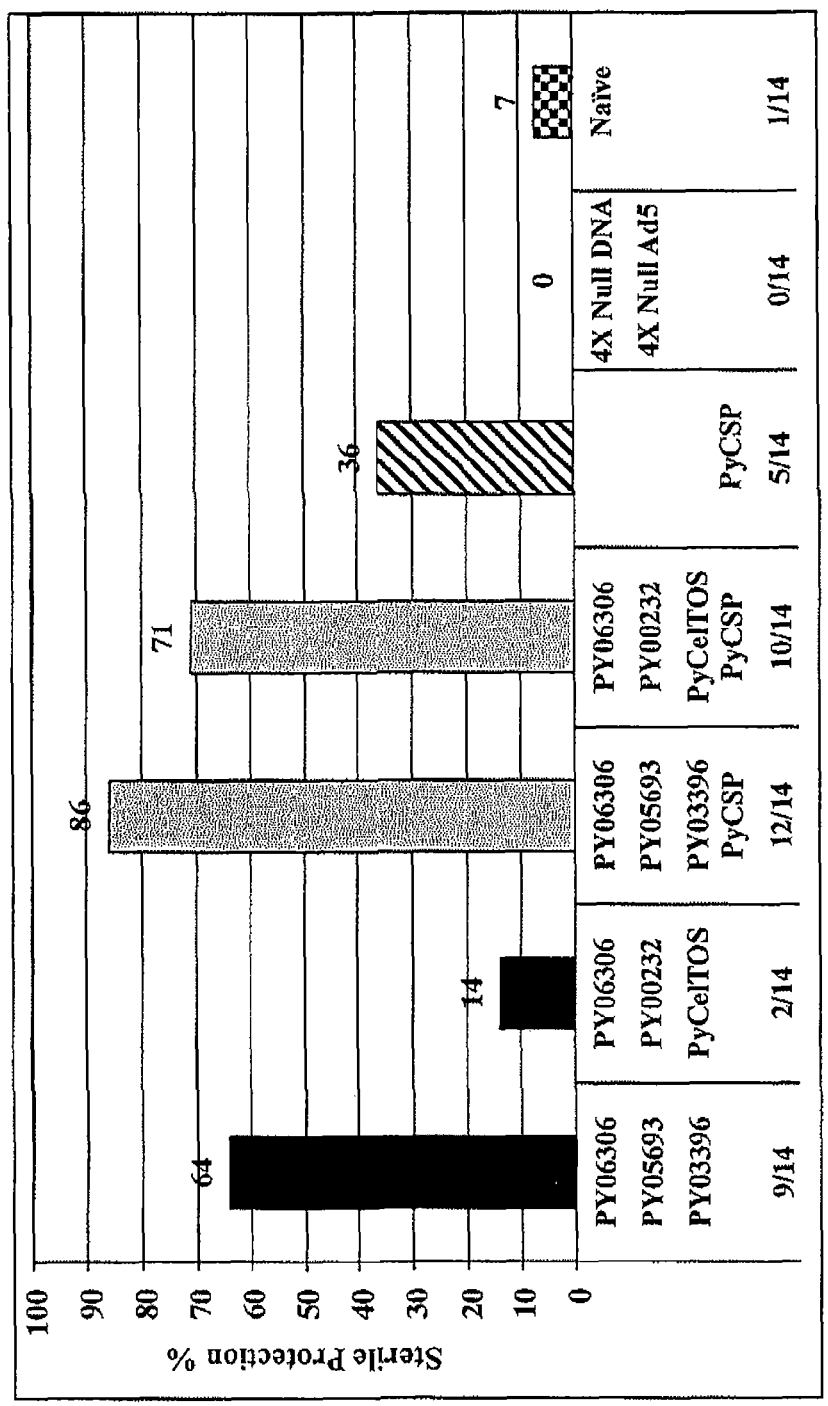
FIG. 1 shows the protection results for a matrix experiment in which fourteen CD1 outbred mice per group were immunized in a prime-boost regimen with a combination of DNA and Human Adenovirus type 5 (Ad5) vectors that express PY03396, PY05693, PY06306, PY00232 and PyCelTOS. Positive control mice were immunized with DNA and Ad5 vectors that express PyCSP. Negative control mice were immunized with 4× relative amount of DNA and Ad5 vector that do not express *P. yoelii* antigen and naïve mice. Gray and black bars indicate antigen combination groups with and without PyCSP, respectively. Hatched and checkered bars represent PyCSP and naïve groups, respectively. The mice were challenged with 300 *P. yoelii* sporozoites and evaluated for parasitaemia by examining Giemsa-stained blood smears up to 14 days post challenge. Numbers at bottom denote number of sterile protected mice per total challenged mice in each group.

The inventor has determined that pre-erythrocytic proteins are critical in conferring protective immunity against malaria. Despite the relatively large number of malaria genes that have been identified, following sequencing of the malaria parasite genome, identification of vaccine candidates has been hampered, to a great extent, by the relatively complex life-cycle of malaria parasite. Furthermore, many genes of the malaria parasite are poorly defined, antigenically, as well as functionally.

Against this backdrop, the inventor decided to undertake high-throughput screening of antigens encoded by numerous genes in order to ascertain potential protective responses. The inventor developed a novel strategy for identifying and testing potential malaria antigens that overcame the difficulties experienced in the prior art. This novel approach included identifying certain traits that the inventor determined would be indicative of potential human vaccine candidates. The inventor then compiled a list of 146 P. yoelii orthologs of P. falciparum genes that were believed to possess these traits. The inventor then designed cloning primers, and conceived of a strategy for cloning the genes and screening by transfection ELISpot. The transfection ELISpot involved transfecting an A20 cell line with the VR1020 vaccine constructs, expressing the antigen, and using these transfected cells to present antigens in the ELISpot assay. This use of ELISpot was a novel strategy for screening antigens. Priority antigens were identified from a large panel of P. falciparum proteins. The priority antigens were evaluated based on a number of criteria judged by the inventor to be relevant to protection against malaria, One such criterion was selecting antigens that are expressed in the sporozoite and liver stages of the malaria parasite; i.e. pre-erythrocytic antigens. Certain antigens among those selected based on this criterion showed protective responses in mice that indicated that orthologs of those genes in humans would encode human antigens useful as potential vaccine formulations. One gene in particular, PY06306, later curated as PY17X_0210400, which is the subject of this disclosure, surprisingly showed dramatic and consistent protection responses indicating that gene as encoding an antigen for which orthologs would be useful as a leading vaccine formulation.

The sequence documented for the PY06306 gene, however, was only partial (479 aa) and originated from the early genome annotation. In order to perform the protection experiments disclosed herein with the full-length antigen (816 aa), the inventor needed to re-clone the gene. A similar situation occurred with the *P. falciparum* (human homolog), which also needed to be re-cloned from what was known in the art. The sequences disclosed in the listing provided herein, used in all of the examples, and reflected in all of the data examples conform to the inventor's corrected version of the gene, rather than what was previously believed in the art to be the relevant sequence.

The invention relates to DNA and amino acid sequences encoding recombinant *Plasmodium falciparum* and *Plasmodium vivax* proteins. Specifically, the invention relates to a highly protective pre-erythrocytic *Plasmodium yoelii* and its *P. falciparum* and *P. vivax* ortholog antigens for use in a malaria vaccine. The relevant sequences can be utilized to express the encoded proteins for use as subunit immunogenic antigens or can be incorporated into vectors suitable for in vivo expression in a host in order to induce an immunogenic response. The antigens can be utilized in combination or singly in immunogenic formulations.

In one embodiment, the immunogenic composition is a DNA-based vaccine. DNA was found to be a viable platform for delivering the immunogenic compositions of the present disclosure. A DNA-based vaccine can be delivered by recombinant viruses, such as Modified Vaccinia Ankara (MVA) attenuated poxvirus, Vesicular Stomatitis Virus (VSV), or GC46 (gorilla adenovirus) viruses. Other human Adenovirus alternatives like these can also be used, such as baculovirus.

In another embodiment, the composition comprises immunogenic proteins. In this embodiment, the proteins can be produced by first inserting the DNA encoding the proteins in suitable expression systems. These include, for example, Adenoviral based systems, a poxvirus based system, or a DNA plasmid system. The expressed and purified proteins can then be administered in one or multiple doses to a mammal, such as humans. In this embodiment, the purified proteins can be expressed individually or DNA encoding specific proteins can be recombinantly associated to form a single immunogenic composition. These immunogenic compositions can then be administered in one or multiple doses to induce an immunogenic response.

One embodiment of the invention relates to recombinant polypeptides expressed as full-length or fragments by heterologous expression systems. Examples of such systems are: *Escherichia coli*, yeast (*Saccharomyces cerevisiae* or *Pichia pastoris*), mammalian cells (HEK293 or CHO cells), baculovirus-infected insect cells, and *Drosophila* S2 stable cells. The recombinant proteins can be incorporated in immunogenic formulations in order to induce an immune response. In this embodiment, the polypeptides can be incorporated singly or in combination. The immunogenic compositions of the invention can also include adjuvants to improve or enhance the immune response elicited by the polypeptides. Suitable adjuvants include ALFQ, a non-toxic formulation comprising a monophosphoryl lipid A-containing liposome composition with saponin.

Adjuvants have traditionally been broadly classified into two major classes according to their component sources, physiochemical properties or mechanisms of action, namely: (i) immunostimulants such as TLR ligands, cytokines, saponins and bacterial exotoxins that directly act on the immune system to increase responses to antigens and (ii) vehicles such as mineral salts, emulsions, liposomes, virosomes and biodegradable polymer microspheres that present vaccine antigens and co-administered immununostimulants to the immune system in an optimal manner. In recent years it has become apparent that many of these vehicles also have a direct effect on the immune system and can be considered immuno stimulants.

Examples of acceptable adjuvants for inclusion with a malaria vaccine include Army Liposome Formulation (ALF) derivatives such as ALF, ALFA (plus aluminum), and ALFQ (plus QS21). Other options include a lipid A derivative and a saponin in a liposome formulation, such as QS21 and 3D-monophosphoryl lipid A (a non-toxic derivative of lipopolysaccharide), other immunostimulants that are similar in structure to LPS, MPL, or 3D-MPL, acylated monosaccharides, saponin derivatives (Quil-A, ISCOM, QS-21, AS02 and AS01), soluble triterpene glycosides, Toll-like receptor 4 (TLR4) agonists, montanides (ISA51, ISA720), immunostimulatory oligonucleotides, and imidazoquinolines. Adjuvants may be prepared in cholesterol-containing liposome carriers.

As used herein, the term "polypeptide" refers to a polymer of amino acids and does not refer to a specific length of the product. Proteins are included within the definition of polypeptides. The term "mer," in conjunction with a number, such as 15-mer, refers to the length of a polypeptide in numbers of amino acids.

As used herein, the proteins may be prepared for inclusion of an effective amount of one or more polypeptides described herein into an immunogenic composition by first expressing the appropriate gene fragments by molecular methods, expression from plasmids or other expression systems such as viral systems and then isolated. A further aspect of the invention is the ability of the proteins to induce an humoral and/or T-cell immune response.

An embodiment of the invention is the incorporation of DNA encoding the polypeptides in vector expression systems, wherein the system permits expression of one or more polypeptides in mammalian host cells, such as in humans to induce an immune response. The expression systems can be DNA plasmids or viral systems. Methods for preparing and administering a DNA vaccine expressing *Plasmodium* proteins are well known in the art.

In another embodiment, derivatives of the proteins can be used in immunogenic compositions. In a variant of this embodiment, the immunogenic derivatives of the *P. falciparum* and *P. vivax* proteins include at least 10 contiguous amino acids of an amino acid sequence of a full length polypeptide comprising an amino acid sequence disclosed herein. Immunogenic derivatives of the polypeptides may be prepared by expression of the appropriate gene fragments or by other methods such as by peptide synthesis. Additionally, derivatives may be a fusion polypeptide containing additional sequence encoding one or more epitopes of the *P. falciparum* polypeptides disclosed herein. In these embodiments, the proteins can be directly incorporated in immunogenic formulations or expressed from DNA plasmids or viral expression systems.

In some embodiments, the *P. falciparum* and *P. vivax* polypeptides include immunogenic derivatives with more than 80% amino acid sequence identity to the sequences disclosed herein. In this context, the term "identity" refers to two or more sequences or subsequences that are the same or have a specified percentage of amino acid residues that are the same, when aligned for maximum correspondence. Where sequences differ in conservative substitutions, i.e., substitution of residues with identical properties, the percent sequence identity may be adjusted upwards to correct for the conservative nature of the substitution.

When the compositions are prepared for administration, they are preferably combined with a pharmaceutically acceptable carrier, diluent or excipient to form a pharmaceutical formulation, or unit dosage form. A "pharmaceutically acceptable carrier" is a carrier, diluent, excipient, and/or salt that is compatible with the other ingredients of the formulation, and not deleterious to the recipient thereof. The active ingredient for administration may be present as a dry powder or as granules; as a solution, a suspension or an emulsion. The composition exists as dry powder prior to reconstitution in a liquid carrier.

Pharmaceutical formulations containing the immunogenic compositions of the invention can be prepared by procedures known in the art using well known and readily available ingredients. The therapeutic agents of the invention can also be formulated as solutions appropriate for parenteral administration, for instance by intramuscular, subcutaneous or intravenous routes. The pharmaceutical formulations of the therapeutic agents of the invention can also take the form of an aqueous or anhydrous solution or dispersion, or alternatively the form of an emulsion or suspension.

Thus, the immunogenic composition may be formulated for parenteral administration (e.g., by injection, for example, bolus injection or continuous infusion) and may be presented in unit dose form in ampules, pre-filled syringes, small volume infusion containers or in multi-dose containers with an added preservative. The composition is suitable for injection intravenously, subcutaneously, or intramuscularly. The active ingredients may take such forms as suspensions, solutions, or emulsions in oily or aqueous vehicles, and may contain formulatory agents such as suspending, stabilizing, and/or dispersing agents. Alternatively, the active ingredients may be in powder form, obtained by aseptic isolation of sterile solid or by lyophilization from solution, for constitution with a suitable vehicle, e.g., sterile, pyrogen-free water, before use.

Additionally, the immunogenic composition may contain formulatory agents that do not occur naturally in the cellular environment in which the peptide is expressed. Such formulatory agents include any surfactants, diluents, solubilizers, emulsifiers, buffers, thickeners, preservatives, detergents, adjuvants, excipients, and antimicrobials that do not naturally occur in the cellular environment in which the peptide is expressed, but nonetheless serve to artificially enhance the bioavailability, effectiveness, delivery, storage, administration, absorption, stability, safety, or function of the peptide in the immunogenic composition before, after, or during administration to a mammal.

Alternately, the immunogenic composition may be provided as a dry powder. A dry powder composition may be prepared by freeze drying, spray drying, and freeze spray drying a solution or suspension containing the polypeptides described herein, and may further optionally include milling or lyophilization with milling. The dry powder may be suitable for direct administration to a patient, such as through inhalation or capsule ingestion, or may be suitable for suspension or reconstitution in a fluid carrier. Dry powder formulations may include physiologically acceptable carrier powders, such as excipients, dispersants, stabilizers, humectants, anti-caking agents, or other additives.

The immunogenic compositions of the present invention, both dry powder and fluid embodiments, may include, as optional ingredients, pharmaceutically acceptable carriers, diluents, solubilizing, or emulsifying agents, and salts of the type that are well-known in the art. Specific non-limiting examples of the carriers and/or diluents that are useful in formulations of the present composition include water and physiologically acceptable buffered saline solutions, such as phosphate buffered saline solutions pH 7.0-8.0. The composition of the present disclosure may also comprise combinations of other agents such as diluents, which may include water, saline, glycerol or other suitable alcohols, wetting or emulsifying agents; buffering agents; thickening agents for example cellulose or cellulose derivatives; preservatives; detergents; antimicrobial agents; and the like.

Where the immunogenic composition is used as a vaccine, the composition comprises an immunologically effective amount of the peptides described herein. An "immunologically effective amount" of an antigen is an amount that when administered to an individual, either in a single dose or in a series of doses, is effective for treatment or prevention of malaria infection. This amount will vary depending upon the health and physical condition of the individual to be treated and on the antigen. Determination of an effective amount of an immunogenic or vaccine composition for administration to an organism is well within the capabilities of those skilled in the art.

A composition according to the invention may be for oral, systemic, parenteral, topical, mucosal, intramuscular, intravenous, intraperitoneal, intradermal, subcutaneous, intranasal, intravaginal, intrarectal, transdermal, sublingual, inhalation or aerosol administration. The composition may be arranged to be administered as a single dose or as part of a multiple dose schedule. Multiple doses may be administered as a primary immunization followed by one or more booster immunizations. The primary immunization may include a single formulation such as a virus (GC46) or DNA vaccine, followed by one or more booster immunizations with single or multiple formulations such as another virus (such as MVA) or recombinant protein. Suitable timings between priming and boosting immunizations can be routinely determined. A composition according to the present disclosure may be used in isolation, or it may be combined with one or more other immunogenic or vaccine compositions, and/or with one or more other therapeutic regimes.

The present disclosure thus provides a method of protecting a human or non-human mammal from the effects of malarial infection comprising administering to the human or non-human mammal a composition described herein. The composition may be a vaccine. The disclosure further provides a method for raising an immune response in a human or non-human mammal comprising administering a pharmaceutical composition described herein to the human or non-human mammal. The immune response is preferably protective. The method may raise a booster response in a patient that has already been primed. The immune response may be prophylactic or therapeutic.

EXAMPLES

Example 1: Identification of E140

A novel, highly protective pre-erythrocytic (PE) *Plasmodium yoelii* (Py) antigen, human orthologs for which are identified for use in a human malaria vaccine. This antigen is identified as PlasmoDB ID 10: PY06306, or PY17X_0210400, PYYM_0211900 or ID: 2121.m00052, depending on the nomenclature used. The antigen is also referred to as E140 or Py E140 in laboratory testing disclosed herein as a shorthand. The novel antigen is highly expressed in the sporozoite, liver, and blood stages of the parasite, and induces $CD8^+$ T cell responses in mice immunized with the *P. yoelii* radiation-attenuated sporozoites (RAS). It generates strong antibody and cellular responses upon antigen-specific vaccine immunizations and sterilely protects between 71%-100% alone and in combination with other antigens of mice from an infectious *P. yoelii* sporozoite and blood stage challenges. First, *P. yoelii* pre-erythrocytic antigens were screened for their reactivity to T cells from RAS-immunized mice as a platform for identifying antigens for vaccine development. This process involved identifying, cloning, generating DNA plasmid (VR1020), screening, and evaluating Py antigens for ability to protect mice. It is well recognized that mouse models are a predictor for success with human orthologs. The gene encoding the PY06306 antigen was identified as a pre-erythrocytic target for vaccine development, and the partial gene was cloned. Experiments then determined that the protein could recall cytokine (IFN-γ) responses from splenocytes generated in mice immunized with the *P. yoelii* RAS. This data provided strong evidence that the PY06306 antigen was involved in the RAS immune response and protection, therefore demonstrating pre-erythrocytic vaccine value in humans.

Example 2: Confirming E140 Protection

Two vaccine reagents were made expressing the PY06306 antigen for protection studies in mice. These reagents were generated with the full-length gene: DNA vaccine in the VR1020 plasmid (PY06306-E140) and adenovirus serotype 5 (AdE1(t.PY06306)E3(10X)E4(TIS1)). The evidence for vaccine potential of the PY06306 antigen is shown in two separate animal matrix studies, intended to assess the ability of the antigen to induce an immune response capable of sterilely protecting mice from an infectious Py sporozoite challenge. The sterile protection was measured by the absence of parasites in the blood of mice examined up to 14 or 17 days post sporozoite challenge. Outbred CD1 mice were immunized with a regimen consisting of a prime with DNA vaccine (100 μg, IM) and a boost with adenovirus serotype 5 constructs ($10^{10}$ PU, IM) 6 weeks later. A 3-antigen combination strategy (named matrix) was adopted to test the PY06306 antigen plus other new Py pre-erythrocytic antigens with and without *P. yoelii* circumsporozoite protein (PyCSP).

The first matrix animal study shown in FIG. 1 revealed two PY06306-containing antigen combinations (groups) yielding significant protection. The first combination induced 64% and 86% sterile protection alone and with PyCSP, respectively. The antigen components of this first combination were E140 (PY06306), E137 (PY05693) and E057 (PY03396). The 86% protection of the 3-antigen mixture combined with PyCSP was twice as high as the PyCSP alone group (43%), indicating a significant enhancement in the efficacy of this gold standard vaccine. The second 3-antigen combination produced 14% and 71% sterile protection alone and with PyCSP, respectively. This second combination consisted of E140 (PY06306) combined with two additional antigens with vaccine potential: Py325 (PY00232) and PyCelTOS (PY17X_1434600). Any or all of these five antigens (PY06306, PY05693, PY03396, PY325, and PyCelTOS) contributes to the protection shown in the corresponding figure; however, PY06306 was the only antigen common to all three antigen combinations, thus requiring a second experiment for the deconvolution of these antigen combinations.

Example 3: Sporozoite Challenge

Figure 2:
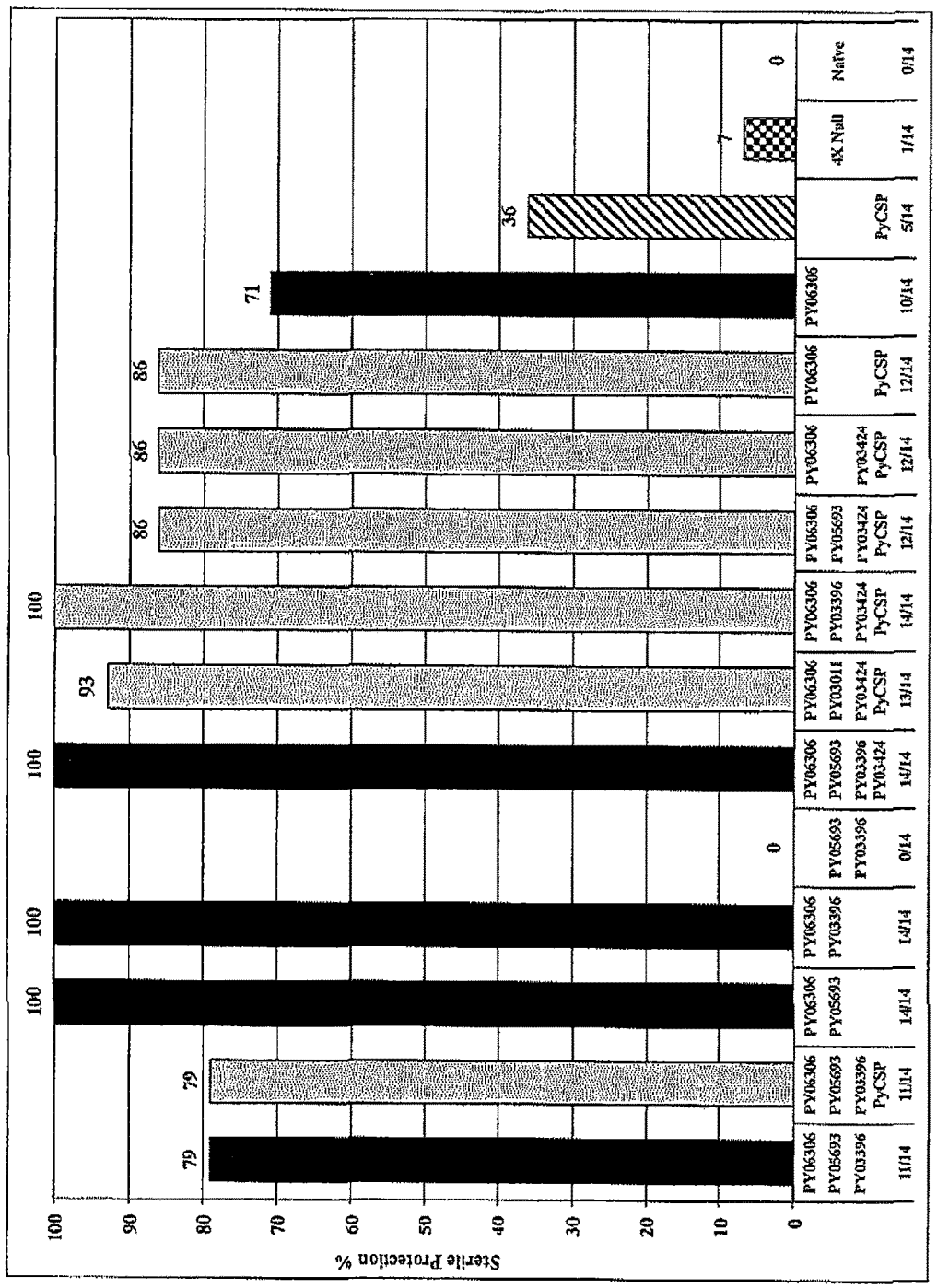
FIG. 2 shows a matrix deconvolution of the experiment evaluating PY06306 and other antigens shown illustrated in FIG. 1. Fourteen CD1 outbred mice per group were immunized in a prime-boost regimen comprising of DNA and Adenovirus type 5 (Ad5) vectors that express PY03396, PY05693, PY06306, PY03424 and PY03011. Positive control mice were immunized with DNA and Ad5 vectors that express PyCSP. Negative control mice were immunized with 4× relative amount of DNA and Ad5 vectors that do not express *P. yoelii* antigen. Gray and black bars indicate antigen combination groups with and without PyCSP, respectively. Hatched and checkered bars represent PyCSP and null-immunized mice, respectively. The mice were challenged with 300 *P. yoelii* sporozoites and evaluated for parasitaemia by examining Giemsa-stained blood smears up to 17 days post challenge. Numbers at bottom denote number of sterile protected mice per total challenged mice in each group.
Figure 3:
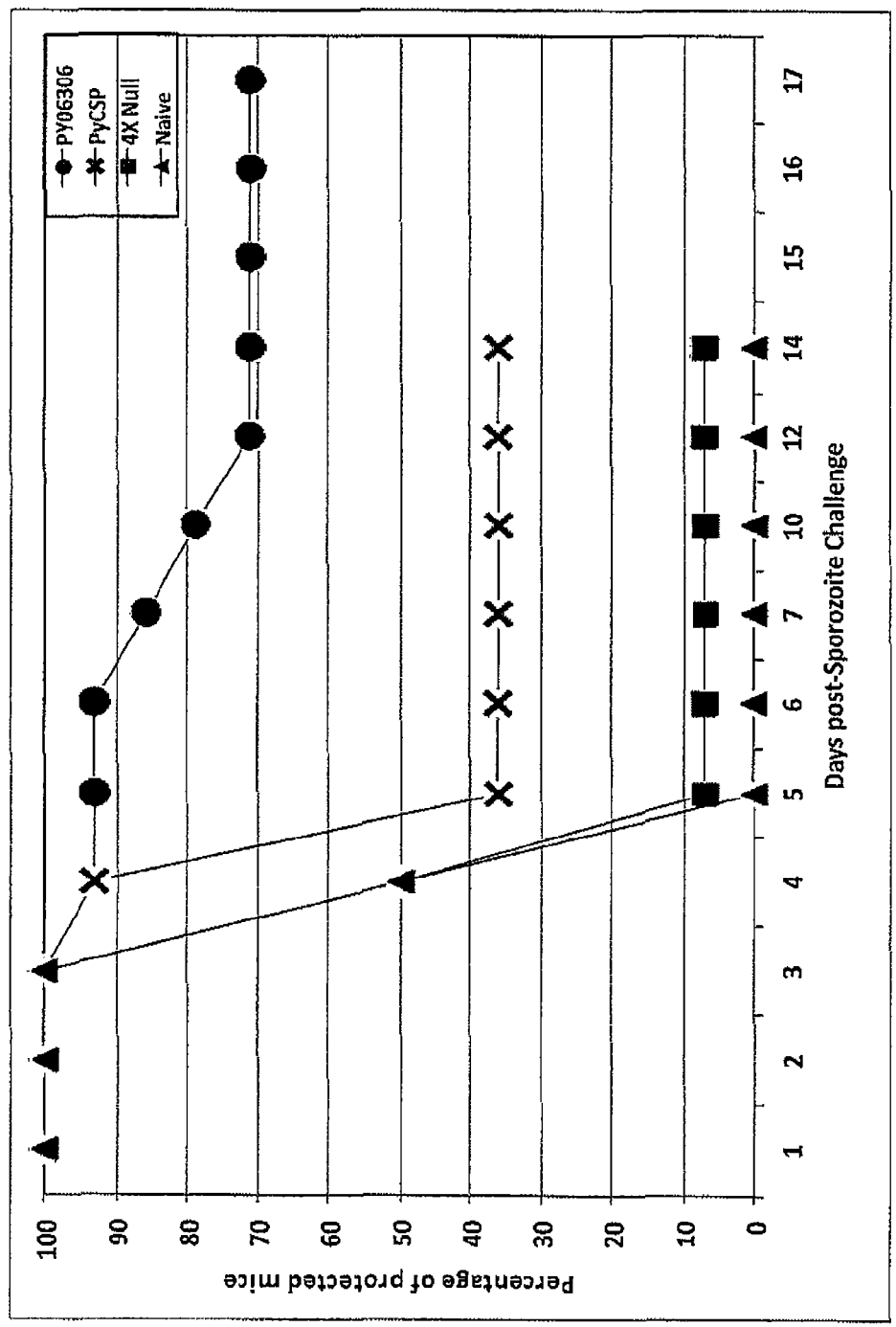
FIG. 3 shows a Kaplan-Meier curve depicting the percentage of protected mice for the time to parasitemia after challenge. Data extracted and analyzed from matrix deconvolution experiment 2. Closed circles indicate CD1 mice immunized with PY06306 antigen alone, Symbols Xs, squares and triangles indicate PyCSP, 4× Null and Naïve mice, respectively. The mice were challenged with 300 *P. yoelii* sporozoites and evaluated for parasitaemia by examining Giemsa-stained blood smears up to 14 (PyCSP, 4× Null and Naïve) or 17 (PY06306) days post challenge.

A second study (Matrix Deconvolution Experiment 2) was designed to evaluate several antigen combinations having the PY06306 as the common denominator antigen. The experimental format and immunizations followed the same regimen as described for the first matrix experiment. FIGS. 1 and 2 show the markedly high efficacy for all antigen combinations that include the PY06306 (E140) antigen, ranging from 71% to 100% of the mice protected. Overall, 89% (137/154) of PY06306-immunized mice were protected from malaria infection. The PY06306 vaccine alone yielded 71% protection, significantly higher compared to 36% for the PyCSP alone group. Furthermore, there was a substantial delay in the onset of parasitaemia of non-protected mice as shown in FIG. 3. Detailed analysis of blood smears data from the PY06306-immunized group shows that three of the four non-protected mice became malaria positive on days 7, 10 and 12 after sporozoite challenge. This is significant when compared to the parasitaemia onset of the PyCSP, 4× Null, and Naive groups, in which all nonprotected mice became malaria positive by day 5 post sporozoite challenge.

Example 4: Antibody Titers

Figure 4:
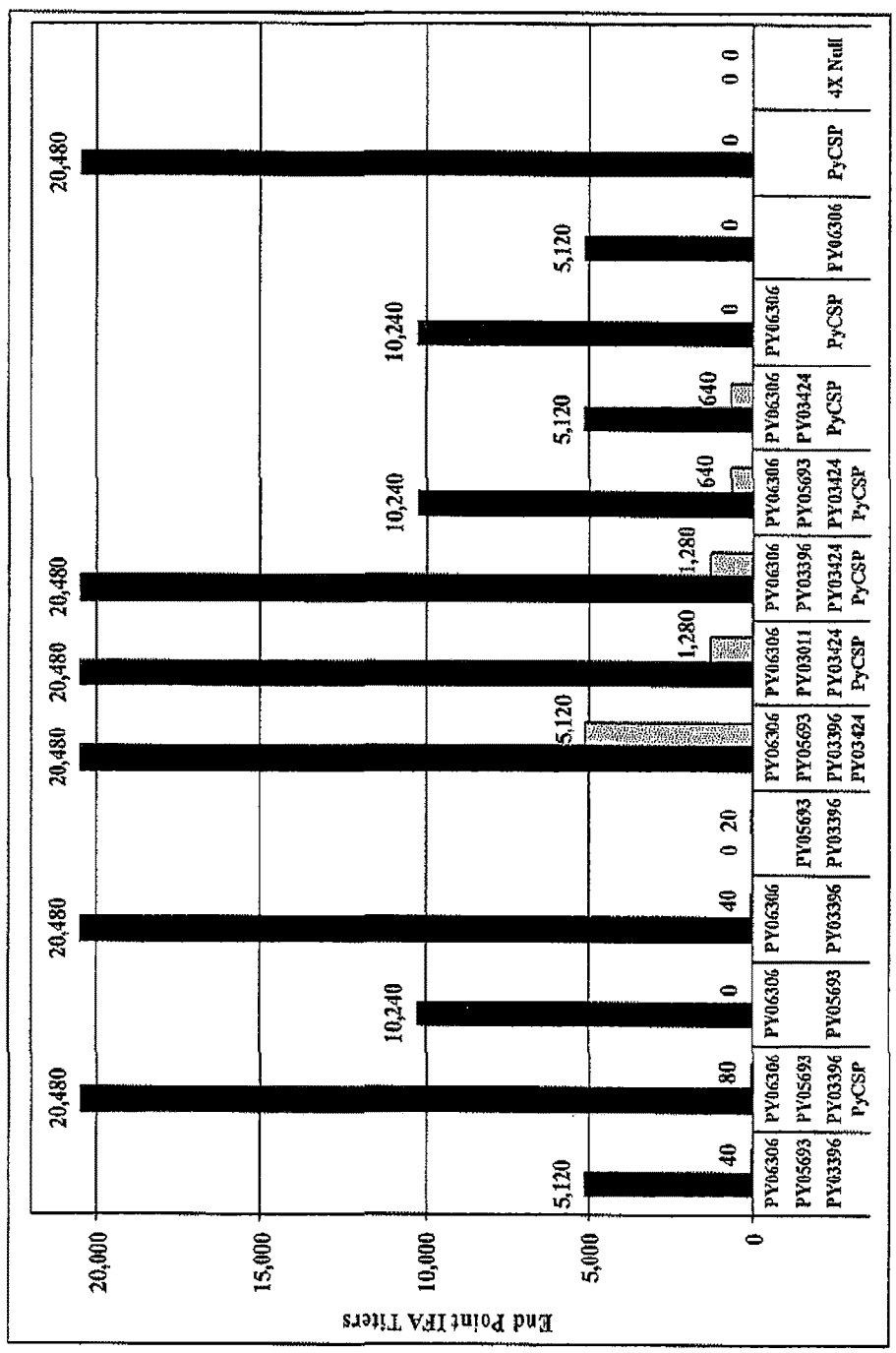
FIG. 4 shows antibody responses for the matrix deconvolution experiment. Endpoint immunofluorescence assay (IFA) titers were measured on *P. yoelii* sporozoite and blood stage parasites. Sera collected one week after Adeno 5 boost was pooled per group of antigen combination and assayed for reactivity on air-dried parasites. Black and gray bars indicate sporozoite and blood stages reactivity, respectively. Positive control antibodies were NYS1 and NYLS3 monoclonal antibodies, respectively. Sera from 4× null and naïve animals were negative.
Figure 5:
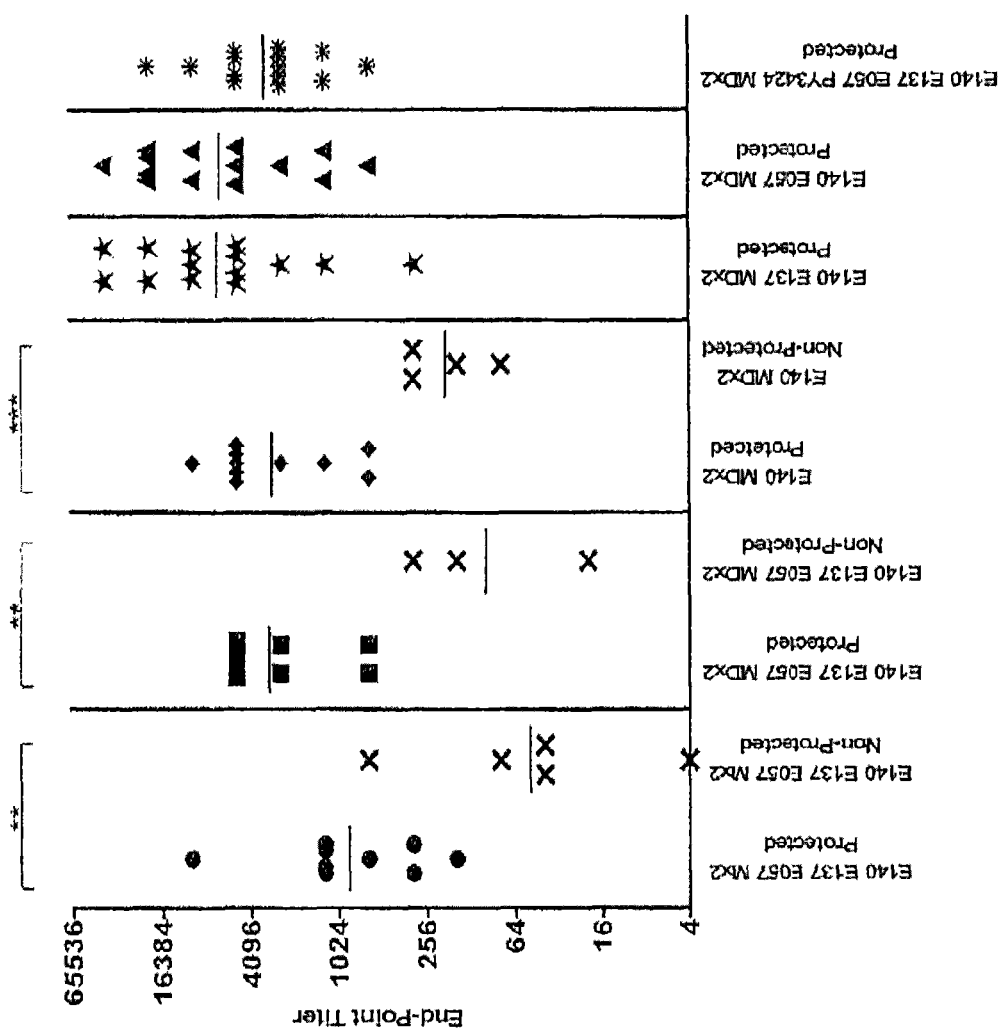
FIG. 5 shows antibody titers of protected and non-protected mice for the matrix deconvolution Experiment shown in FIG. 4. Endpoint Immunofluorescence (IFA) titers were measured against *P. yoelii* sporozoite for individual mice for six PY06306 (E140)-containing groups of mice. One group from matrix experiment 2 (Mx2); E140, E137, E057 combination (closed circles) and five groups from matrix deconvolution experiment 2 (MDx2); E140, E137, E057 combination (closed squares), E140 alone (closed diamonds), E140, E137 combination (closed stars), E140, E057 combination (closed triangles), and E140, E137, E057, PY3424 combination (closed asterisks). All protected mice are displayed by closed symbols and all non-protected by the X symbol. Mann-Whitney non-parametric test indicates statistical significance;, p<0.005 and*, p=0.001.
Figure 6:
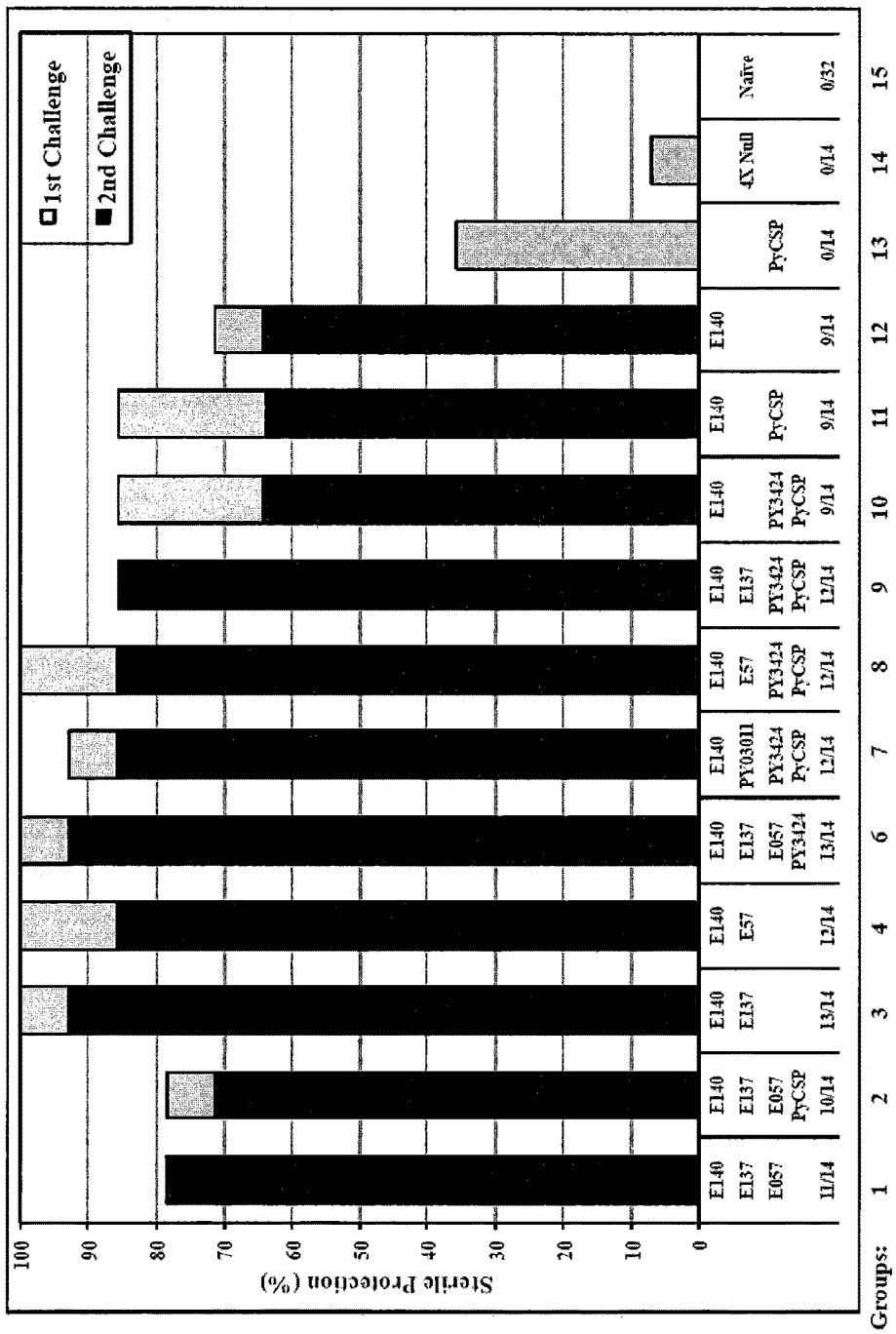
FIG. 6 shows continued protection at 11 weeks for the deconvolution study shown in FIG. 2. Sterilely protected mice were rested for 11 weeks and then challenged with 200 *P. yoelii* sporozoites. Protection was measured by examining Giemsa-stained blood smears up to 17 days post challenge.

The PY06306 antigen induces high antibody titers to *P. yoelii* sporozoite stages and low antibody levels to blood stages depending on the individual mouse. This evidence is shown in FIG. 4 (PY06306 group) listing immune fluorescence (IFA) antibody titers to both sporozoite and blood stage parasites measured in pooled sera from mice in the Matrix Deconvolution Experiment 2. In summary, anti-sporozoite antibodies were detected in all groups immunized with PY06306, including combinations, which supports the immunogenicity of PY06306 antigen. Titers range from 1:5,120 to 1:20,480. Antibodies induced by the *P. yoelii* PY06306 immunization cross-reacts to *P. berghei* sporozoites. The detection of high antibody titers (1:5,120) in mice immunized with PY06306 alone demonstrates that the PY06306 antigen induces antibodies to sporozoites.

Two important observations based on a review of the data are: (i) the absence of protection (0%) and the lack of antibody response for the group of antigens without PY06306 (PY03396 and PY05693) in FIG. 2. This confirms that the PY06306 is the main, if not the only component of these combinations inducing protection. The other (ii) is the anti-sporozoite antibody response induced specifically by the PY06306 antigen. The comparison of the anti-sporozoite IFA titers for the protected versus non-protected mice strongly indicates that the antibodies detected in these mice correlate with the protection outcome. All protection studies were performed under animal protocols D02-09 and 14-IDD-13. The results of the protection studies validate the role of PY06306 orthologs as valuable components for a malaria vaccine.

Example 5: Spleen and Liver Analysis

Further studies confirmed that in spleen, >10% CD8+ T cells expressing IFNγ and lower (<0.6%) CD4+ T cells in PY06306-immunized mice. A range of 5% to 16.2% in liver was observed. High efficacy of protection continued 11 weeks after a second sporozoite challenge. The T cell depletion indicates that high levels of E140-specific T cells are not required for protection in mice. Additionally, PY06306 immunization induces high levels of CD8+ T cells expressing IFNγ in the spleen liver. Anti-PY06306 sera transfer to both CD1 and BALB/c mice significantly delayed the onset of parasitemia. E140-sera recipient mice also had significantly lower IFA titers compared to protected mice immunized with PY06306. PY06306 sera collected prior to sporozoite challenge reacts to sporozoites only. However, after challenge some protected mice developed antibodies positive to blood stage by IFA.

PY06306 sterilely protects up to 100% of CD1 and BALB/c mice from a blood stage challenge (FIG. 11) Immunization with PY06306 prevents blood infection and delays onset of detectable parasitemia in 88% (30/34) of non-protected mice. Additionally, transfer of anti-PY06306 antibodies to naïve mice significantly delays infection. High levels of CD8+ T cells expressing IFNγ in are found in spleens and livers of PY06306-immunized mice. Depletion did not reduce sterile protection. PY06306-specific IFA antibody titers correlate with protection.

Example 6: In Vivo T Cell Depletion

Figure 9:
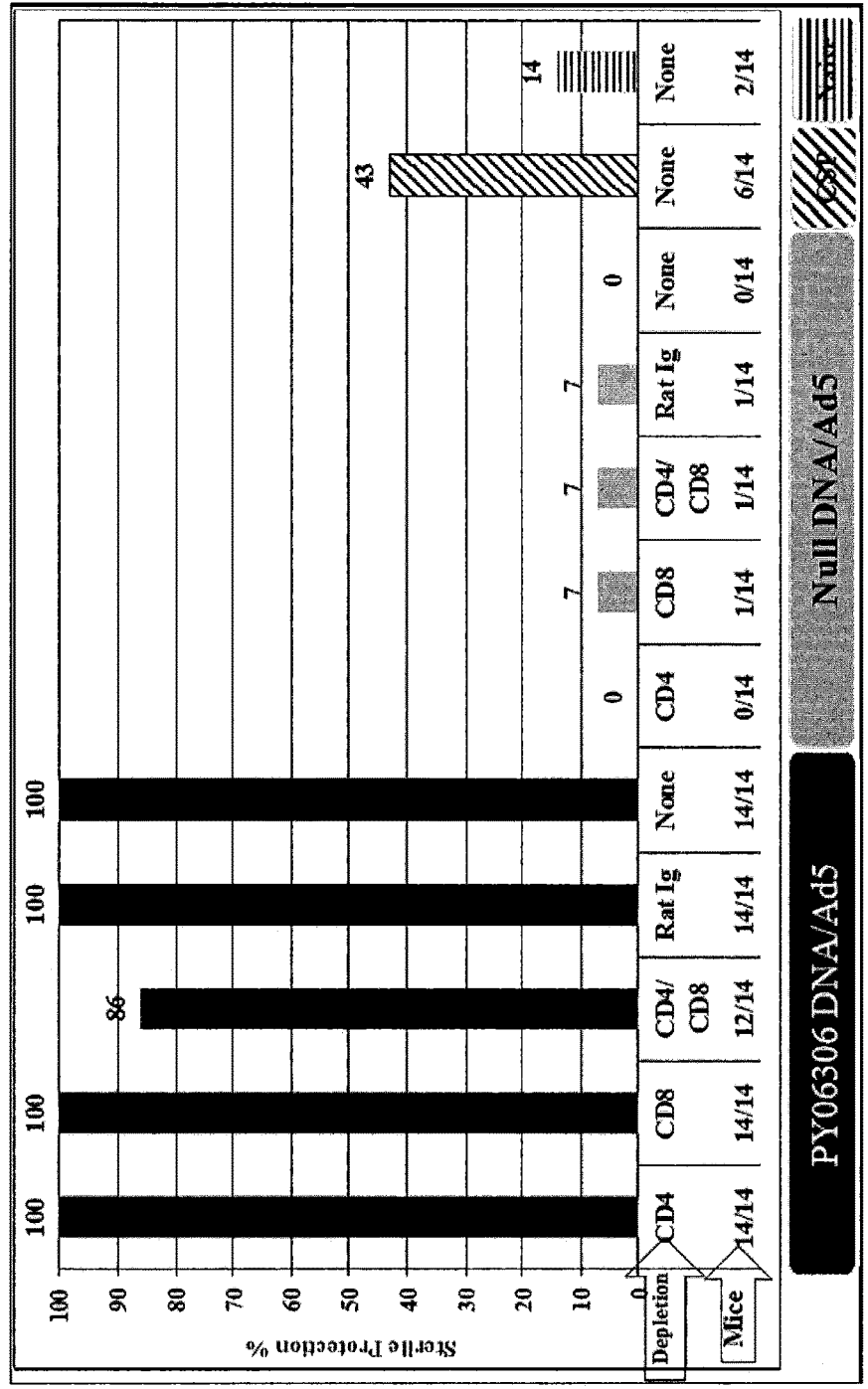
FIG. 9 shows the results of an in vivo T cell depletion experiment in mice. CD1 outbred mice were immunized with PY06306 DNA and boosted with Adeno 5 vaccines, $CD4^+$, $CD8^+$, $CD4^+/CD8^+$ T cells depleted (black bars) before and after challenge with 300 *P. yoelii* sporozoites. Rat Ig and no depletion groups were used as positive controls. Groups of null-immunized mice (gray bars) were also depleted the same way and used as negative controls. PyCSP (diagonal bar) and Naïve (stripe bar) were experimental positive and negative controls. Arrows indicate the type of depletion and the number of mice sterile protected out of the number immunized. Challenged mice were evaluated for parasitaemia by examining Giemsa-stained blood smears up to 19 days post challenge.

FIG. 9 shows the results of a study on in vivo t-cell depletion. Several groups of outbred CD1 mice were immunized. T cell depletions were performed by injection of T cell-specific monoclonal antibodies following standard protocols. Mice were then challenged with 300 P. yoelii sporozoites and protection assessed by the absence of parasites in thin blood smears up to 19 days after challenge. All PY06306-immunized mice that had their T cells depleted were protected, confirming that both CD4+ and CD8+ T cells are not required for the PY06306 protection. One non-protected mouse from the CD4/CD8 group had malaria detected in the blood 13 days post sporozoite challenge while all other mice had positive smears on day 5. A total of 68 protected mice out 70 were immunized, a 97% overall efficacy. This study confirmed the surprising mechanism that protection induced by a pre-erythrocytic antigen against a sporozoite challenge does not rely on T cells.

Example 7: Sera Transfer Studies

Figure 10A:
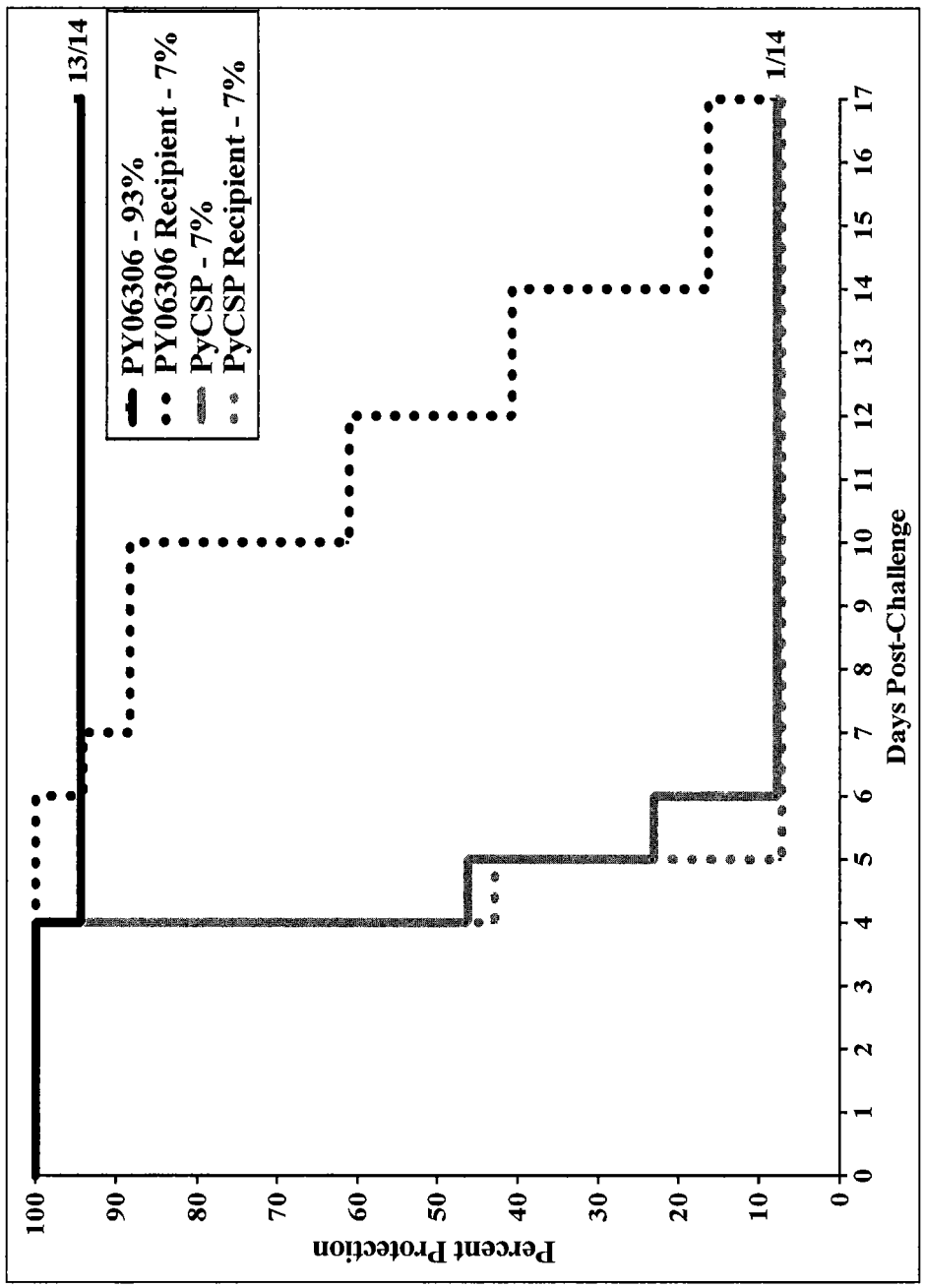
FIGS. 10A and 10B shows sera transfer studies in CD1 and BALB/c mice.
Figure 10B:
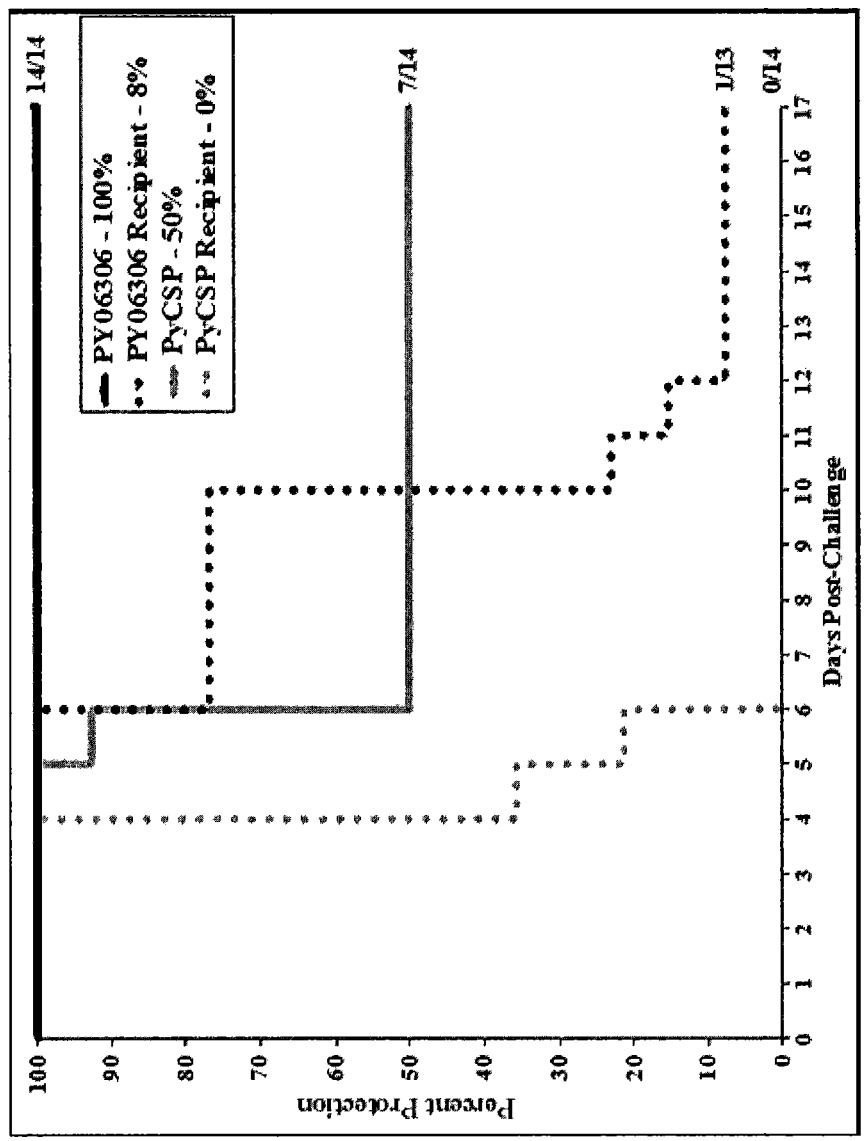

FIGS. 10A and 10B shows sera transfer studies in CD1 and BALB/c mice. This study confirmed the role of antibodies in the protection induced by PY06306 (E140). The study design followed standard sera transfer protocols, where sera from PY06306-immunized CD1 and BALB/c mice were harvested, transferred to naïve animals (1:1 ratio), and then challenged with P. yoelii sporozoites. Sera transfers took place over 2 days; 24 hours and 6 hours before the sporozoite challenge. The protection results are shown in FIG. 10A for CD1 mice and FIG. 10B for BALB/c mice. FIGS. 10A and 10B show that no sterile protection was transferred with sera (7% (1 out 14) of CD1 and 0% (0 out 14) of BALB/c) from mice immunized with PY06306 vaccine. There was a statistically significant delay in the onset of parasitemia on all non-protected mice from the PY06306 sera recipient (dotted line) as compared to any other group in the same study (Mantel-Cox ***, p=0.0001). This confirms that the anti-PY06306 antibodies have an effective impact on the parasite development in the blood play a role in the protection. Significantly lower antibody titers in the recipient CD1 (1:2,560) and BALB/c (1:575) mice and compared to the donor CD1 (1:7,994) and BALB/c (1:18:549) mice explain why these mice were not protected from the challenge.

Example 8: Detection of PY06306-Specific CD8 T Cells in Spleen and Liver

PY06306-specific CD8 T cells are found in the spleens and livers of PY06306-immunized and naïve mice. Due to the fact that PY06306 is a large molecule, 15 mer overlapping peptides were divided into two pools spanning the entire protein; Pool A containing peptides from the N-terminal and Pool B from the C-terminal of PY06306. T cells were measured by flow cytometry gated for CD8+ cells expressing Interferon gamma (IFNγ) and expressed as a percentage of the total T cell population. The data shows that only peptides from Pool A were able to recall IFNγ CD8 cells confirming that PY06306 T cell epitopes are likely restricted to the N-terminal of the antigen. Very high levels of CD8+ T cells expressing IFNγ, were detected for both spleens (average 18%) and livers (average 11%) of PY06306-immunized mice. For intracellular cytokine staining, splenocytes and liver-resident T cells were prepared from PY06306- and Null-immunized mice using standard protocols, followed by stimulation for six hours with a final concentration of 2 μg/ml of PY06306 (E140) peptide pools A and B. Data were acquired using a LSRII flow cytometer (BD Biosciences) and analyzed using FlowJo (Tree Star Inc.).

Example 9: PY06306 Induces Protection in BALB/c Mice

PY06306 antigen effectively protects BAB/c strains of mice against a sporozoite challenge. Fourteen BALB/c mice per group were immunized with a dose of DNA and boosted with Adenovirus 5 encoding PY06306, PY06306+PyCSP, and PyCSP. Null-immunized and naïve were used as negative control groups of mice. All mice were challenged with 100 infectious P. yoelii sporozoites and parasitaemia monitored for 17 days after challenge by Giemsa-stained thin smears. Upon challenge all (100%) PY06306-immunized mice were sterilely protected (PY06306 and PY06306+ PyCSP) whereas 57% of PyCSP were protected. Thus PY06306 can protect an inbred strain of mice, and mixing with PyCSP antigen does not inhibit the PY06306 protection.

Example 10: PY06306 Induces Protection Against a Blood Stage Challenge

Figure 11:
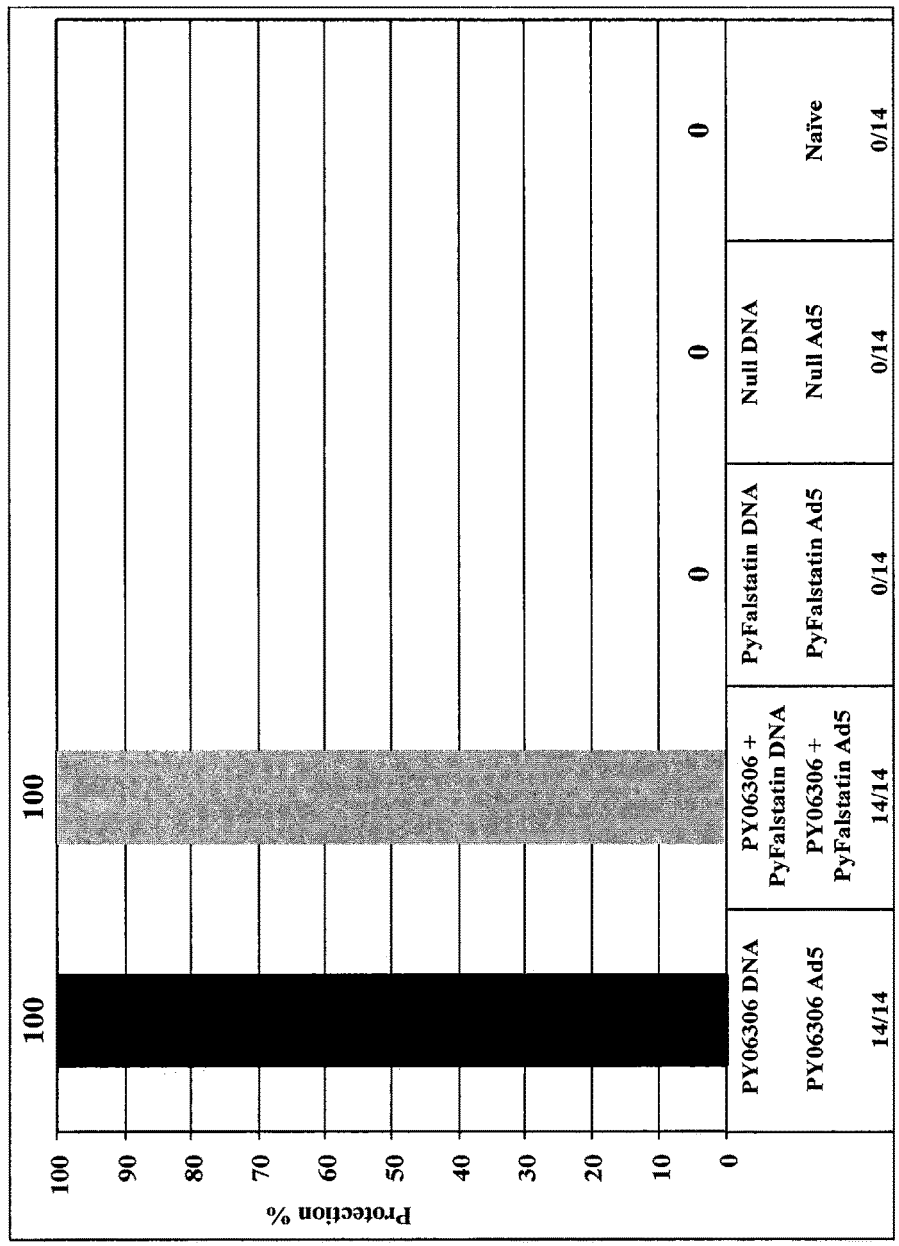
FIG. 11 shows PY06306 protection against a blood stage challenge. Fourteen CD1 mice per group were immunized with a dose of DNA and boosted with Adenovirus 5 expressing PY06306 (black bar), PY06306+PyFalstatin (gray bar), and PyFalstatin alone). Null-immunized and naïve were used as negative control groups of mice. PyFalstating is also known as PY03424. All mice were challenged with 10,000 infected P. yoelii-infected erythrocytes and parasitaemia monitored for 17 days after challenge by Giemsa-stained thin smears.

FIG. 11 shows PY06306 protection against a blood stage challenge. PY06306 antigen alone and in combination with PyFalstatin protects mice against a stringent challenge with 10,000 blood stage parasites. In this study, mice immunized with PY06306 alone and in combination with PyFalstatin and challenged with P. yoelii-infected erythrocytes. Both groups of mice were 100% sterilely protected (black and gray bars). PyFalstatin antigen is also known as PY03424. The protection against a blood stage challenge provides a second level of defense induced by the PY06306 vaccine, a valuable feature for a malaria vaccine.

Example 11: Protection with Lower and Single Dose of Codon-Optimized PY06306 Ad5

Figure 12:
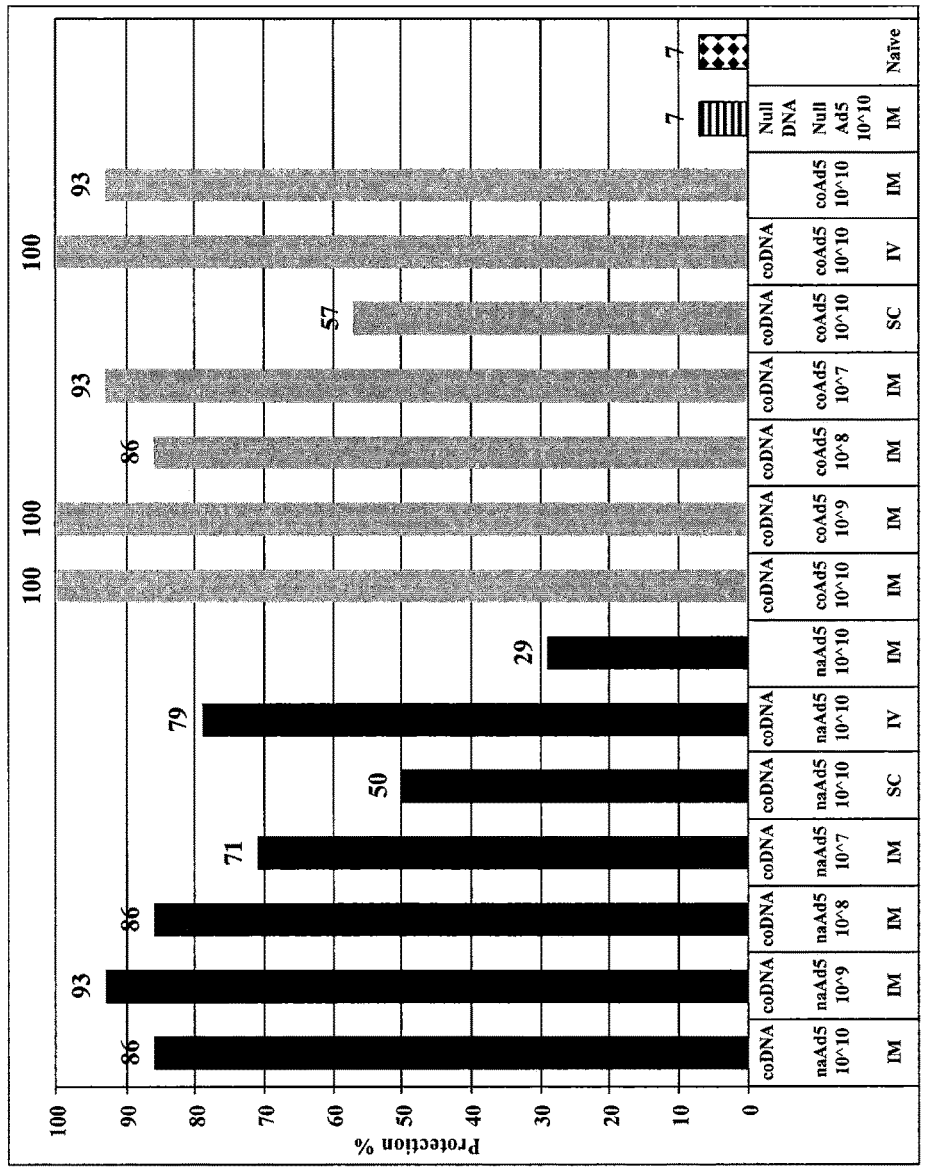
FIG. 12 shows protection with mammalian codon-optimized Adenovirus 5 in a chart comparing native (na) and codon-optimized (co) PY06306 and route of immunizations. CD1 mice (14 per group) were primed with a co E140 DNA and boosted with either native PY06306 Adeno 5 (black bars) or mammalian co PY06306 Adeno 5 (gray bars). Both Adeno 5 constructs were administered intramuscular (IM) in decreasing doses from 10^10, 10^9, 10'8, and 10^7 PU. Two additional groups of mice were boosted with Ad5 administered either subcutaneously (SC) or intravenously (IV). Two additional mice groups were not primed with DNA vaccine and instead immunized with a single IM dose of either na or co PY06306 Ad5 two weeks before challenge. Null-immunized (stripe bar) and Naïve (checkered bar) mice are negative controls. All mice were challenge with 300 P. yoelii sporozoites, parasitaemia were monitored over 18 days by thin blood smears stained with Giemsa.
Figure 14:
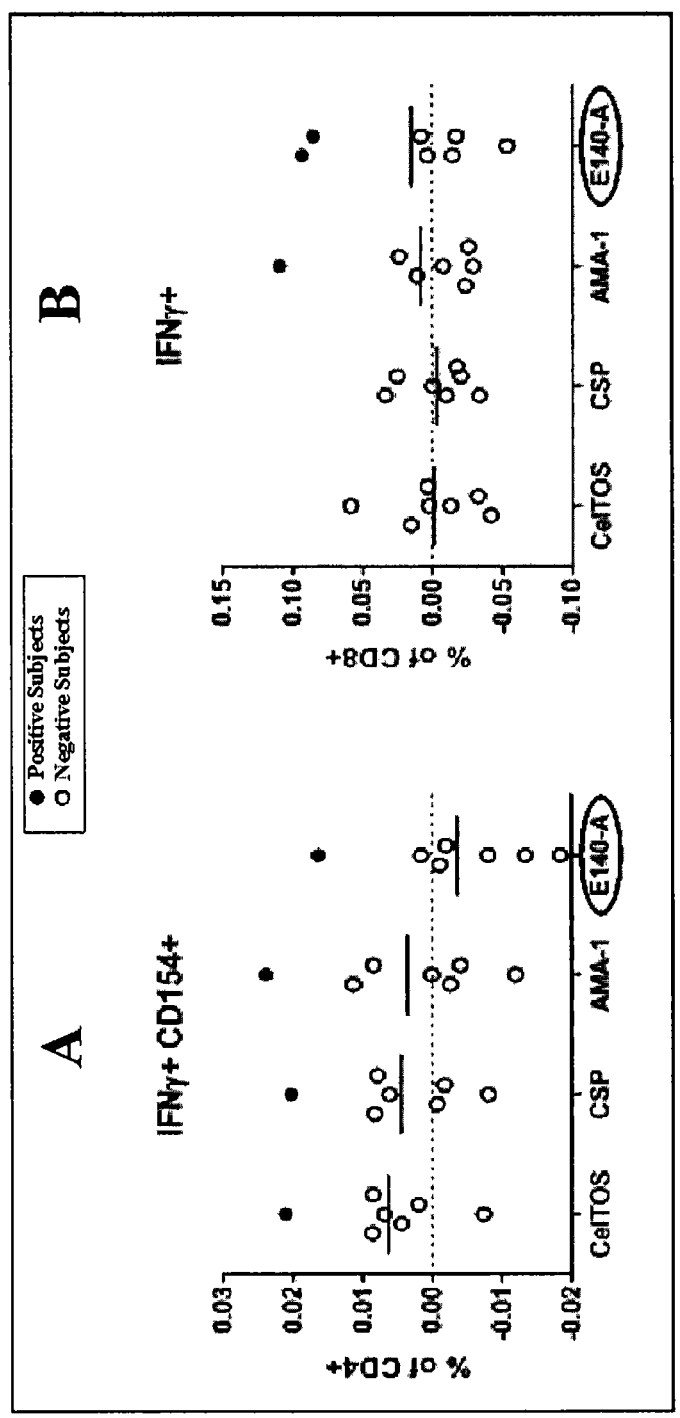
FIG. 14 shows that the P. falciparum E140 (PFA0205w) is naturally immunogenic in humans. T cell responses to PFA0205w (PfE140 or PF3D7_0104100) by P. falciparum radiation attenuated sporozoites (RAS)-immunized human subjects. PBMCs were stimulated with overlapping 15 mer peptide PFA0205w pools A for 21 h with brefeldin A and stained for viability, phenotypic (CD14, CD19, CD3, CD4, and CD8), and intracellular functional markers (including IFN-γ and CD154). The background subtracted frequencies of CD4$^+$ T cells producing IFN-γ and intracellular CD154 (A) and CD8$^+$ T cells producing IFN-γ(B) are shown. Positive responses for PFA0205w pool A (filled symbols) in both experiments were identified as those exceeding two standard deviations from the average of the negative control (DMSO stimulated) samples.

FIG. 12 shows protection with codon-optimized Adenovirus 5. This study evaluated an Adenovirus 5 construct made with codon-optimized (co) PY06306 gene designed for expression in mammalian cells. The change in the PY06306 native codon sequence did not alter the amino acid sequence expressed by the Ad5 virus, A study examined and compared the in vitro expression of the PY06306 protein expressed by the native (na) and codon-optimized (co) Adenovirus 5 constructs. After probing with mouse polyclonal sera, the coPY06306 Ad5 expresses much higher levels of PY06306 protein compared to the native construct. In the first groups of mice, the boosting dose was titrated for both native (na) and codon-optimized PY06306 Ad5 ranging from 10^10, 10^9, 10^8 and 10^7 PU per dose. All mice in these eight groups were primed with the same coPY06306 DNA vaccine dose (100 μg) and boosted with varying doses of either naPY06306 (black bars) or coPY06306 (gray bars) Ad5 construct intramuscular (IM). The overall efficacy indicates that the co PY06306 Ad5 vaccine induces higher protection in CD1 mice (100%, 100%, 86% and 93%) compared to the na PY06306 had lower protection (86%, 93%, 86% and 71%) for the same Ad5 doses. The study also compared subcutaneous (SC) and intravenous (IV) routes for Ad5 administration. SC route yielded similar protection levels for both na and co PY06306 vaccine (50 and 57% respectively). The IV route for the co PY06306 Ad5 resulted in 100% sterile protection, while the na provided 79%. The IV route for na PY06306 Ad5 yielded 79% sterile protection, while subcutaneous yielded 50% protection. Mice groups immunized with a single dose of coPY06306 Ad5 induced 93% sterile protection compared to 29% for the naPY06306 vaccine. These mice received no DNA vaccine priming. All protection studies were performed under animal protocols D02-09 and 14-IDD-13.

Example 12: Human *P. falciparum* is Immunogenic in Mice

FIG. 13 shows that *P. falciparum* PFA0205w (E140 ortholog) is immunogenic in mice. Four vaccine reagents were generated for PFA0205w (aka PF3D7_0104100), these are: VR1020 DNA vaccine construct, human Adenovirus 5 construct, protein expression plasmids pEU-E01-GST, and pEU-E01-His. DNA vaccine and Ad5 were produced in large scale for mice immunizations. Recombinant proteins were produced in small-scale by the wheat germ cell-free system at NMRC. Both CD1 and BALB/c mice were immunized using a variety of prime-boost regimens as shown in FIG. 13. The Ad5 prime and recombinant protein boost was the most immunogenic regimen, inducing IFA titers up to 1:4,000 to both *P. falciparum* blood and sporozoite stage parasites. A single dose of PFA0205w Adeovirus 5 induce antibodies to parasites. This confirms that PFA0205w as a single dose of recombinant virus (Adenovirus 5) or as a prime-boost with an Ad5-protein regimen are viable as vaccine formulations.

Example 13: *P. falciparum* E140 (PFA0205w) is Immunogenic in Humans

FIG. 14 shows that the *P. falciparum* E140 (PFA0205w) is immunogenic in humans. T cells from individual subjects immunized with radiation-attenuated sporozoites (RAS) were able to respond to stimulation with PFA0205w peptide pool (A). The peptide mixture contained 15 mer overlapping peptides covering most of the N-terminus region of PFA0205w protein. Since the protein is large, the peptides were divided into two pools; pool A covering the N-terminus and pool B for the C-terminus of the PFA0205w protein. The data in both graphs indicated that the imuunizations with the attenuated sporozoite vaccine induce both CD4 and CD8 T cells in humans. CD4+ and CD8+ T cells play a role in the PFA0205w-induced protection against pre-erythrocytic parasites. There are high levels of *P. yoelii* E140 responses in the spleen and livers of E140-immunized mice.

Example 14: PFA0205w is Expressed in Schizonts and Localized in the Surface and Cytosol of Sporozoites The PFA0205w antigen is expressed at both the sporozoite and schizont stages of *P. falciparum*. The IFA reactivity was obtained using CD1 mice serum generated by priming with PFA0205w Adenovirus 5 and boosting with recombinant PFA0205w protein. The serum was positive for 36-hour *P. falciparum* erythrocytic schizonts and negative for early rings and trophozoites. The subcellular localization of PFA0205w antigen in sporozoites was determined by immuno electron microscopy (EM). The analysis of micrographs showed that PFA0205w antigen is localized in both at the surface and in the cytosol of *P. falciparum* sporozoites. Immuno fluorescence and immuno electron microscopy showed reactivity of serum from CD1 mice immunized with PFA0205w Adeno 5 and boosted with recombinant PFA0205w protein. Air-dried IFA slides were made with NF54 *P. falciparum* parasites about 36 hours after invasion of red blood cell. IFA was performed with 1:500 serum dilution and developed with a FITC-labeled goat anti-mouse Ig. For immuno EM, *P. falciparum* sporozoites-containing salivary glands were isolated from infected mosquitoes. Fixed glands were embedded, sectioned, mounted on electron microscopy grids and stained using same serum and colloidal gold-labeled anti-mouse antibodies. Micrographs confirmed that the PFA0205w antigen is localized in both at the surface and in the cytosol of *P. falciparum* sporozoites.

Example 15: PVX_081555 (PvE140) is Expressed in *P. vivax* Sporozoites

FIG. 15 shows that PVX_081555 (PvE140) is expressed in *P. vivax* sporozoites. *Anopheles dirus* mosquitos were fed blood through a membrane feeder from patients infected with *P. vivax* malaria. Fourteen days after the membrane feeding the mosquito salivary glands were extracted from 100 mosquitos. The salivary glands were crushed in a microcentrifuge tube containing phosphate-buffered-saline with a pestle and to liberate *Plasmodium vivax* sporozoites. The salivary gland debris-sporozoite mixture was then centrifuged to remove the mosquito salivary gland debris and the *P. vivax* sporozoites were transferred from the supernatant to a new microcentrifuge tube. The extracted *P. vivax* sporozoites were counted and 1×106 sporozoites were digested with 1 ug of molecular biology grade trypsin at 37 degrees Celsius for 18 hours. After digestion the trypstic sporozoite peptides were desalted over a C8 reversed phase column and lyophilized. The lyophilized tryptic peptides were subjected to multi-dimensional-protein-identification technology (MudPIT) to identify *P. vivax* sporozoite proteins that might be vaccine candidates. Tandem mass spectra generated from *P. vivax* sporozoites were searched against a combined *Anopheles-Plasmodium vivax* protein sequence database using the Sequest algorithm. Output files from the Sequest search were loaded into the Scaffold protein viewer. Sequences matching the *Anopheles* proteome were subtracted using the Scaffold program to highlight proteins that specifically matched the *P. vivax* proteome. Scaffold software was used to compare the abundance of each of the *P. vivax* sporozoite proteins identified by MudPIT. Protein abundance was defined by the Scaffold "quantitative value" which normalizes the abundance of mass spectra matching a given protein to that protein's molecular weight. 256 high-confidence *P. vivax* proteins were identified in this MudPIT experiment. *P. vivax* E140 (PVX_081555) was the 39th most abundant *P. vivax* sporozoite protein and the 5th most abundant membrane-associated protein sequenced. In comparison, the CSP vaccine antigen, that is also associated with the parasite membrane, was the 5th most abundant protein overall and the most abundant membrane-associated protein in the sample. This result illustrates that *P. vivax* E140 is among the most abundant membrane-associated proteins in the parasite. E140's membrane association and abundance therefore make it an exceptional target of the humoral response.

I claim:

1. An immunogenic composition comprising
    (a) a recombinant polypeptide;
        wherein the recombinant polypeptide comprises SEQ ID NO:3, or a recombinant polypeptide that comprises at least 10 contiguous amino acids of SEQ ID NO:3 and has at least 85% sequence identity with SEQ ID NO:3;
    (b) a pharmaceutically acceptable carrier; and
    (c) an adjuvant;
    further comprising one or more additional recombinant polypeptides, wherein the one or more additional recombinant polypeptides comprise an amino acid sequence selected from the group consisting of SEQ ID NO.6, SEQ ID NO.7, SEQ ID NO.8, SEQ ID NO.9, or a recombinant polypeptide that comprises at least 10 contiguous amino acids of SEQ ID NO. 6, SEQ ID NO. 7, SEQ ID NO. 8, and SEQ ID NO. 9 and has at least 85% sequence identity with one of SEQ ID NO. 6, SEQ ID NO. 7, SEQ ID NO. 8, and SEQ ID NO. 9.

2. An immunogenic composition comprising:
    (a) a recombinant polypeptide;
        wherein the recombinant polypeptide comprises SEQ ID NO:3, or a recombinant polypeptide that comprises at least 10 contiguous amino acids of SEQ ID NO:3 and has at least 85% sequence identity with SEQ ID NO:3;
    (b) a pharmaceutical acceptable carrier; and
    (c) an adjuvant.

3. The immunogenic composition of claim 2, wherein the recombinant polypeptide comprises at least 10 contiguous amino acids of SEQ ID NO:3 and has at least 92% sequence identity with SEQ ID NO:3.

4. The immunogenic composition of claim 3, wherein the recombinant polypeptide is an E140 antigen of a *Plasmodium falciparum* strain.

5. The immunogenic composition of claim 4, wherein the strain selected from the group consisting of 3D7, UGT5.1, 7G8, *Mali*, UGPA, HB3, Santa Lucia, IGH-CR14, FCH/4, NF135/5-C10, Tanzania, FVO, and Dd2.

6. The immunogenic composition of claim 2, wherein the recombinant polypeptide comprises SEQ ID NO:3.

7. The immunogenic composition of claim 2, wherein the adjuvant is selected from the group consisting of an Army Liposome Formulation (ALF) derivative, a lipid A derivative, a saponin in QS21, a saponin in 3D-monophosphoryl-lipid A, lipopolysaccharide (LPS), monophosphoryl lipid A (MPL), 3-O-deacylated monophosphoryl lipid A (3DMPL), acylated monosaccharides, a saponin derivative, soluble triterpene glycosides, Toll-like receptor 4 (TLR4) agonists, montanide ISA51, montanide ISA720, immunostimulatory oligonucleotides, and imidazoquinolines.

8. The immunogenic composition of claim 7, wherein the ALF derivative is selected from the group consisting of ALF, ALF plus aluminum (ALF A), and ALF plus QS21 (ALFA).

9. The immunogenic composition of claim 7, wherein the saponin derivative is selected from the group consisting of Quil-A, Immune stimulating complexes (ISCOM), QS-21, AS02, and AS01.

10. The immunogenic composition of claim 2, which is a dry power, granules, a solution, a suspension, or an emulsion.

11. The immunogenic composition of claim 10, which is a dry powder.

12. The immunogenic composition of claim 11, wherein the dry powder is suitable for administration to a mammal upon suspension or reconstitution in a pharmaceutically acceptable carrier.

13. The immunogenic composition of claim 10, wherein the solution is an aqueous solution.

14. The immunogenic composition of claim 10, wherein the solution is an anhydrous solution.

15. The immunogenic composition of claim 2, which is formulated for oral, systemic, parenteral, topical, mucosal, intramuscular, intravenous, intraperitoneal, intradermal, subcutaneous, intranasal, intravaginal, intrarectal, transdermal, sublingual, inhalation, or aerosol administration.

16. The immunogenic composition of claim 2, further comprising one or more formulatory agents selected from the group consisting of surfactants, diluents, solubilizers, emulsifiers, buffers, thickeners, preservatives, detergents, adjuvants, excipients, and antimicrobials;
    wherein the formulatory agents that do not naturally occur in the cellular environment in which the peptide is expressed.

17. The immunogenic composition of claim 2, which is formulated as an ampule, a pre-filled syringe, a small volume infusion container, or in multi-dose containers with an added preservative.

18. The immunogenic composition of claim 17, which is formulated as a pre-filled syringe.

* * * * *

SEQUENCE LISTING

<160> NUMBER OF SEQ ID NOS: 9

<210> SEQ ID NO 1
<211> LENGTH: 816
<212> TYPE: PRT
<213> ORGANISM: Plasmodium yoelii

<400> SEQUENCE: 1

```
Met Gly Asp Val Asp Asn Val Leu Ile Ser Ile Lys Lys Ile Glu Ser
1               5                   10                  15

Ile Lys Ser Gln Leu Asn Gln Leu Asn Lys Ile Ile Gln Asn Glu Phe
            20                  25                  30

Gly Ser Tyr Cys Gly Arg Lys Asn Arg Ser Ile Asn Leu Glu Ile His
        35                  40                  45

His Asn Glu Phe Asp Lys Ser Ile Phe Lys Arg Leu Tyr Ser Ser Trp
50                  55                  60

Arg Met Glu Asp Leu Asn Asn Phe Asn Gly Lys Ser Val Ile Lys Ile
65                  70                  75                  80

Met Glu Arg Asn Pro Tyr Val Ile Phe Phe Phe Phe Ile Met Ile
                85                  90                  95

Phe Ile Ile Val Tyr Leu Ile Ser Phe Ile Leu Tyr Thr Lys Trp Phe
                100                 105                 110

Lys Lys Leu Leu Lys Lys Phe Ser Asn Ser His Lys Asn Asn Lys Asp
            115                 120                 125

Lys Glu Glu Asp Trp Val Lys Lys Asn Lys Ala Tyr Arg Asn Ser Asn
        130                 135                 140

Ser Thr His Gly Thr Ile Asn Lys Asp Asn Tyr Asn Gln Glu Leu Asp
145                 150                 155                 160

Glu Leu His Asn Ser Asp Glu Asn Gly Glu Asn Ser Asn Val Ile Asn
                165                 170                 175

Ile Val Lys Lys Arg Ala Tyr Asn Leu Val Ile Asn Leu Ile Val Cys
                180                 185                 190

Ser Phe Leu Ile Cys Leu Ile Phe Leu Gly Ile Trp Thr Ile Phe Ile
            195                 200                 205

Phe Ala Asp Thr Gln Lys Gly Ile Asn Met Asn Ile Cys Gly Leu Ser
        210                 215                 220

Lys Thr Val Glu Gln Phe Leu Ile Asp Lys Cys Pro Asp Thr Lys Asn
225                 230                 235                 240

Val Asn Pro Gln Cys Tyr Ser Leu Glu His Val Ile Asn Asp Ala Val
                245                 250                 255

Ser Val Met Asn Gln Tyr Gln Leu Thr Lys Glu Phe Val Lys Asn Lys
                260                 265                 270

Thr Asn Leu Asn Lys Asn Lys Gly Leu Pro Ile Val Leu Lys Tyr Gln
            275                 280                 285

Thr Gly Phe Asn Met Leu Ala Lys Leu Arg Asp Asn Ile Asp Lys Asn
        290                 295                 300

Val Lys Lys Leu Glu Asn Gly Tyr Leu His Thr Tyr Pro Val Leu Thr
305                 310                 315                 320

Lys Leu Arg Phe Thr Leu Asp Glu Ile Val Ser Lys Gly Glu Asn Leu
                325                 330                 335

Leu Asn Gln Ala Glu Ser Ile Ile Asp Ser Ser Lys Glu Glu Ile Gly
                340                 345                 350

Lys Ile Phe Asn Asn Val Asp Asn Ala Ile Ala Asn Thr Val His Asn
            355                 360                 365
```

-continued

Asn Val Pro Ser Leu Ser Ser Lys Ile Ser Gly Leu Gly Ile Tyr Ile
370                 375                 380

Lys Lys Gln Asp Glu Asn Leu Lys Ile Arg Tyr Ile Leu Asn Lys Phe
385                 390                 395                 400

Thr Val Thr Met Ile Ile Leu Ser Ile Val Ile Leu Leu Phe Ser Leu
            405                 410                 415

Leu Val Leu Ile Gly Met Leu Ser Tyr Met Tyr Phe Leu Ile Arg Gly
                420                 425                 430

His Ser Ile Asn Glu Lys Phe Phe Ser Lys Leu Leu Gly Phe Phe Ser
            435                 440                 445

Gly Thr Phe Gly Phe Leu Ala Ile Ile Ile Leu Ile Ile Gly Thr Ala
450                 455                 460

Leu Leu Ser Leu Ser Val Leu Gly Gly Thr Ser Cys Ile Ile Ser Asp
465                 470                 475                 480

Arg Ile Leu Lys Asn Glu Phe Thr Phe Asp Phe Leu Ser Glu Asn Lys
                485                 490                 495

Ile Gly Tyr Cys Leu Gln Asn Pro Asp Glu Ser Ile Ile Asn Lys Asn
            500                 505                 510

Ile Val Lys Lys Tyr Ala Asn Thr Leu Asp Ser Leu Asn Thr Asn Asp
        515                 520                 525

Ile Tyr Asn Ser Val Glu Gly Tyr Ser Gly Tyr Phe Asp Lys Ile Lys
    530                 535                 540

Asp Glu Tyr Lys Gln His Ser Lys Ile Ile Asn Glu Asn Met Trp Ile
545                 550                 555                 560

Ile Ile Pro Thr Asp Asn Asn Lys Tyr Val Lys Asn Val Lys Ser Asp
                565                 570                 575

Ile Ile Lys Lys Ser Leu Leu Gly Thr Cys Leu Thr Lys Glu Ser Ala
            580                 585                 590

Gln Phe Glu Glu Tyr His Leu Met Gly Thr Asp Ala Tyr Met Lys Tyr
        595                 600                 605

Ile Asn Lys Phe Gly Leu Leu Asn Asn Tyr Glu Met Cys Phe Glu Asp
    610                 615                 620

Pro Ser Cys Glu Asn Asn Asp Arg Lys Tyr Asn Ile Asn Tyr Asn Ser
625                 630                 635                 640

Lys Val Thr Asp Pro Lys Tyr Leu Asp Val Lys Arg Asn Arg Val Met
                645                 650                 655

Leu Tyr Gln Asp Ser Asp Phe Asp Asn Val Leu Glu Val Phe Ile Leu
            660                 665                 670

Lys Ser Lys Ile Asn Asn Asp Lys Ile Phe Asn Ile Ser Asp Leu Asp
        675                 680                 685

Glu Thr Lys Lys Glu Asn Ile Thr Trp Arg Glu Tyr Thr Pro Lys Asn
    690                 695                 700

Gly Ala Gly Glu Asn Lys Lys Ser Ile Val Gln Thr Tyr Phe Glu Lys
705                 710                 715                 720

Ala Ile Glu Tyr Met Lys Phe Glu Asn Val Leu Thr Leu Leu Lys Glu
            725                 730                 735

Val Asn Asn His Ile Asn Ser Phe Lys Asn Val Ile Glu Lys Ala
        740                 745                 750

Asn Ser Leu Val Asp Asn Thr Asn Cys Ser Arg Phe Ile Asn Val Leu
            755                 760                 765

Thr Asn Ile Arg His Asn Tyr Cys Asp Asn Gly Ile Leu Lys Leu Thr
770                 775                 780

Arg Leu Ser Val Ile Leu Ile Ser Cys Gly Phe Val Ser Phe Cys Leu

|     |     |     |     |     |     |     |     |     |     |     |     |     |     |     |
| --- | --- | --- | --- | --- | --- | --- | --- | --- | --- | --- | --- | --- | --- | --- |
| 785 |     |     |     | 790 |     |     |     | 795 |     |     |     | 800 |     |     |
| Trp | Tyr | Leu | Phe | Leu | Phe | Phe | Trp | Ile | Tyr | His | Gln | Met | Lys | Ile | Ile |
|     |     |     |     |     | 805 |     |     |     |     | 810 |     |     |     |     | 815 |

<210> SEQ ID NO 2
<211> LENGTH: 2451
<212> TYPE: DNA
<213> ORGANISM: Plasmodium yoelii

<400> SEQUENCE: 2

```
atgggagacg ttgacaatgt gttaataagt atcaaaaaaa tagaatcaat aaaaagccaa      60
ttaaaccagt taaacaaaat tatacaaaat gaatttgggt cttattgtgg gcgaaaaaat     120
agaagtataa atcttgaaat acatcataat gaatttgata aaagtatatt caacgttta      180
tattcatcat ggagaatgga agatcttaat aattttaacg ggaaaagtgt tataaaaata     240
atggaaagaa atccatatgt tatatttttt ttttttttta taatgatttt tattattgtt     300
tatttaattt catttatttt gtatactaaa tggtttaaaa aattattaaa aaaattttcg     360
aattcacaca aaataataa agataaagaa gaagattggg taaaaaaaaa taaagcttat     420
agaaattcta atagcacaca tggtactatt aataaggata attataatca ggaacttgat     480
gagcttcata atagtgatga aaatgaagaa atagtaatg ttataaatat tgtaaaaaag     540
agagcttata atttagtaat taatttgata gtttgttctt tcttatttg tcttattttt     600
ttgggaattt ggacaatatt tattttgca gatacacaaa aaggaattaa tatgaatatc     660
tgtggattat caaaaacagt tgaacagttt cttattgata aatgccccga cacaaaaaat     720
gtaaatccac aatgttattc tttagagcat gttattaatg atgctgtttc agtaatgaat     780
cagtatcaac tcaccaaaga atttgttaaa aataaaacga atttgaacaa gaataagggc     840
ttgcctattg ttttaaagta ccaaaccgga ttcaacatgc tagcaaaact tagagacaac     900
atagataaaa atgttaaaaa attagagaac ggatatcttc acacatatcc agttttaaca     960
aaacttagat ttactttgga tgaaattgtt tcgaagggag agaatctatt aaatcaggct    1020
gaatctatta ttgattcttc aaaagaagaa attggaaaaa tattcaataa tgtagataat    1080
gctatagcta atactgtaca taataatgtt ccgtctttat catcaaaaat aagtggatta    1140
ggaatatata taaaaaaaca agacgaaaat ttaaaaatac gatatatatt aaataaattt    1200
acagttacaa tgataatttt aagtatagtc atattattat tttcattact tgtgttaata    1260
ggaatgttat cttatatgta ttttttaata agaggccatt caataaatga aaaattttt    1320
tcaaaattac ttggtttttt tagtggaaca tttggatttt tagcaattat aattttaata    1380
ataggtacgg cattattaag tttatctgtt ttgggtggaa caagttgtat tatatctgat    1440
cgaatattaa aaaatgaatt tactttgat ttttttaagcg aaaataaaat tggttattgt    1500
ttacagaatc cagatgaatc tattattaat aaaaatattg taaaaaaaata tgcaaacact    1560
cttgactctt taaatacaaa tgatatatat aatagtgttg aaggctatag tggttatttt    1620
gataaaatta aggatgaata taacaacat tctaaaatta taatgaaaaa tatgtggata    1680
attattccta cagataataa taaatatgta aaaaatgtta atcagatat tattaaaaaa    1740
tcattattag gaacatgttt aacaaaagaa agtgcccaat tgaagagta tcatcttatg    1800
ggaacagatg cttatatgaa atatatataat aaatttggtt tgctaaataa ttatgagatg    1860
tgttttgaag acccatcatg tgaaataac gacagaaaca acaatatcaa ttataactct    1920
aaagttacag acccaaaata tcttgatgtt aaacgtaata gagtcatgct ttatcaagat    1980
```

-continued

```
agcgattttg ataatgtact tgaagtgttc atattaaaat caaaaattaa taatgataaa      2040
atttttaata ttagcgattt agatgaaaca aagaaggaaa atataacatg gagagaatat      2100
acaccaaaaa atggagccgg agaaaataaa aaatctattg ttcaaacata ttttgagaaa      2160
gctattgaat atatgaaatt tgaaaatgtt ttaactttac ttaaagaagt taataatcat      2220
ataaattcat ttaaaaatgt tattattgaa aaagctaatt cattagtaga taatacaaat      2280
tgtagtagat ttattaatgt actaactaat ataagacata attattgtga caatggaatt      2340
ttaaaattaa ctcgattatc agtcatactt atttcatgtg gatttgtttc cttttgtctt      2400
tggtaccttt cctttttttt ttggatatac catcaaatga agattatttg a               2451
```

<210> SEQ ID NO 3
<211> LENGTH: 791
<212> TYPE: PRT
<213> ORGANISM: Plasmodium falciparum

<400> SEQUENCE: 3

```
Met Val Asp Phe Asn Asp Leu Ser Val Glu Leu Lys Lys Thr Glu Leu
1               5                   10                  15

Ile Lys Glu Asp Leu Arg Asn Leu Ser His Ile Ile Asn Asn Glu Phe
            20                  25                  30

Ser Tyr Phe Cys Gln Asn Glu Asn Lys Asn Val Ser Phe Asn Asn Asn
        35                  40                  45

Ile Ser Ser Tyr Tyr Asn Asp Ile Phe Ser Lys Ser Thr Leu Asn
    50                  55                  60

Asn Leu Tyr Thr Ser Trp Lys Leu Glu Asp Phe Ser His Phe Asp Phe
65                  70                  75                  80

Ser Ser Ile Leu Asp Ile Leu Lys Arg Asn Gln Tyr Val Met Cys Ser
                85                  90                  95

Ile Tyr Phe Leu Leu Ile Phe Ser Cys Ile Tyr Phe Leu Thr Leu Leu
            100                 105                 110

Leu Tyr Thr Lys Cys Ile Lys Thr Thr Leu Lys Lys Trp Phe Cys Arg
        115                 120                 125

Tyr Cys Ser Glu Asn Ile Asn Glu Asn Asn Ser Asn His Asn Glu Gln
    130                 135                 140

Arg Thr Val Leu Gln Asn Val Ile Asn Lys Ser Cys Tyr Phe Ile Thr
145                 150                 155                 160

Tyr Ser Ser Ile Ile Cys Leu Leu Leu Phe Leu Leu Leu Ser Gly Ile
                165                 170                 175

Thr Tyr Met His Tyr Phe Ile Lys Thr Lys Lys Gly Ile His Ser Asn
            180                 185                 190

Ile Cys Asn Ile Tyr Thr Arg Leu Asp Lys Phe Leu Leu Asn Lys Cys
        195                 200                 205

Leu Asp Pro Lys Lys Val Asp Thr Ser Cys Tyr Ser Ala Glu His Ile
    210                 215                 220

Leu Asn Asp Leu Ser Ser Ile Leu Glu Glu Tyr Lys Lys Val Lys Gln
225                 230                 235                 240

Gln Ala Lys Asp Asp Thr Leu Leu Asp Glu Asn Thr Pro Phe Pro Leu
                245                 250                 255

Leu Glu Arg Tyr Ile Thr Thr Phe Asn Lys Leu Asn Val Leu Lys Asn
            260                 265                 270

Asn Ile Asn Lys Asn Asn Thr Thr Leu Glu Asn Glu Tyr Phe His Thr
        275                 280                 285

Tyr Pro Ala Leu Lys Gly Ile Ser Glu Thr Leu Thr Thr Ile Ile Ser
```

```
            290                 295                 300
Glu Gly Asn Lys Asn Phe Gly Asn Ala Arg Asn Val Ile Lys Glu Val
305                 310                 315                 320

Lys Ser Thr Ile Lys Tyr Ser Phe His Thr Val Asp Glu Thr Ile Arg
                325                 330                 335

Asn Val Phe Lys Asp Ser Val Pro Lys Ile Thr Gly Leu Ile Thr Gln
                    340                 345                 350

Ala Gly Lys Ser Ile Lys Gly Ile Asn Asn Lys Tyr Lys Ile Lys Glu
                355                 360                 365

Arg Ile Pro Lys Tyr Thr Asn Ile Ile Leu Leu Thr Asn Ile Ile Leu
        370                 375                 380

Leu Leu Pro Pro Phe Leu Ile Leu Leu Gly Ile Ile Phe Met Ile
385                 390                 395                 400

Phe Ile Leu Met Gly Tyr Ile Gln Lys Asn Asn Asn Phe Phe Ile Lys
                405                 410                 415

Leu Phe Gly His Phe Ser Ala Tyr Phe Gly Leu Leu Thr Ile Ile
                420                 425                 430

Leu Ser Phe Gly Ile Leu Phe Leu Ser Thr Ser Val Ile Gly Gly Thr
        435                 440                 445

Ser Cys Ile Leu Ser Glu Arg Ile Leu Lys Asn Glu Leu Arg Phe Asp
    450                 455                 460

Ile Leu Asn Asn Thr Leu Ile Asp Tyr Cys Ile Lys Asn Glu Ser Ala
465                 470                 475                 480

Pro Leu Ile Asp Asp Ile Thr Thr Ser Phe Val Ala Lys Ile Asn
                485                 490                 495

Ser Phe Asp Thr Gly His Ile Asp His Asn Ile Asn Glu Tyr Glu Lys
                500                 505                 510

His Phe Thr Ile Leu Lys Glu Ser Phe His Lys Ser Leu Lys Phe
        515                 520                 525

Met Asp Tyr Ile Trp Ile Val Ile Met Lys Arg Glu Asn Asn Thr Phe
        530                 535                 540

Leu Asn Arg Ile Arg Thr Glu Gln Val Lys Lys Ser Leu Leu Ile Thr
545                 550                 555                 560

Gly Ile Ile Asn Glu Asn Ile Lys Tyr Glu Asn Met Glu Ala Ile Gly
                565                 570                 575

Ile Arg Ser Tyr Leu Thr Thr Leu Asn Lys Ile Phe Pro Glu Asn
                580                 585                 590

Asn Gly Lys Ile Cys Phe Asn Asp Ile Ile Cys Glu Lys Glu Asn Asn
                595                 600                 605

Thr Tyr Asn Ile Thr Glu Asn Ser Lys Thr Thr Asp Gln Lys Tyr Arg
        610                 615                 620

Asn Ile Arg Asp Gly Met Asp Glu His Leu Arg Asn Asp Leu Asp Ala
625                 630                 635                 640

Ile Val Gln Leu Phe Val Tyr Lys Ala Arg Ile Leu Lys Glu Asn Ile
                645                 650                 655

Phe Asp Ile Asn Asp Leu Asp Ser Asn Glu Lys Asn Lys Ile Gly Trp
                660                 665                 670

Ser Glu Tyr Thr Pro Arg Asn Ile Asn Gly Thr Gln Lys Lys Ser Ile
                675                 680                 685

Ile Asn Thr Phe Leu Val Asn Val Ile Glu Ser Ile Asn Phe Ser Glu
        690                 695                 700

Ile Ile Asn Phe Phe Asp Lys Met Arg Asp Gln Phe Asn Val Leu Lys
705                 710                 715                 720
```

```
Asp Leu Ile Leu Leu Lys Ile Asp Thr Leu Thr Glu Asn Thr Lys Cys
            725                 730                 735

Asn Lys Leu Val Lys Glu Leu Ile Asn Val Arg Lys Asp Tyr Cys Asn
        740                 745                 750

Asn Val Val Leu Asn Leu Ser Thr Leu Ser Val Tyr Leu Ile Ile Phe
    755                 760                 765

Ser Ile Thr Ser Phe Leu Leu Trp Tyr Leu Phe Leu Phe Leu Trp Phe
770                 775                 780

Tyr Tyr Asn Ile Lys Pro Ser
785                 790

<210> SEQ ID NO 4
<211> LENGTH: 2375
<212> TYPE: DNA
<213> ORGANISM: Plasmodium falciparum

<400> SEQUENCE: 4
```

| | | | | | |
|---|---|---|---|---|---|
| atggtagact | tcaacgattt | aagcgttgaa | ctaaaaaaaa | cagaattaat | aaaagaggac      60 |
| ctgagaaatc | taagccatat | aataaataat | gaatttagtt | acttttgtca | aaatgaaaac     120 |
| aagaacgtat | ctttcaacaa | taatattagt | agttattata | atgatgatat | attttctaaa     180 |
| agtacattaa | ataatttata | tacatcttgg | aaattagaag | attttctca  | ttttgatttc     240 |
| agtagtattt | tagatatatt | aaaaagaaat | caatatgtta | tgtgtagtat | atatttcctc     300 |
| ctaattttt  | cttgtatcta | ttttttaaca | ttattattat | atacaaaatg | tataaaaaca     360 |
| acgttaaaaa | aatggttctg | tagatattgt | agtgaaaata | taaatgaaaa | taatagtaat     420 |
| cataatgaac | aaagaacagt | attacaaaat | gttataaata | aatcatgtta | ttttattact     480 |
| tattcatcta | taatctgtct | tttattattt | cttctacttt | ctggaattac | atatatgcat     540 |
| tattttataa | aaacaaaaaa | aggaatacat | tctaatattt | gtaatattta | tacaaggctt     600 |
| gataaattct | tattaaataa | atgtctagat | ccaaaaaaag | ttgataacct | gtgttattca     660 |
| gctgaacata | tattgaatga | tctttcttcc | atattggaag | aatataaaaa | ggtgaagcaa     720 |
| caagcaaagg | acgacacgtt | gcttgacgag | aacactccct | tccccctact | cgaaagatac     780 |
| attacaacgt | tcaataagct | aaatgtacta | aaaaacaata | taaataaaaa | taacacaaca     840 |
| ctcgaaaacg | aatacttcca | cacatatcca | gccctcaaag | gaatcagcga | aacactaaca     900 |
| accattatta | gtgaaggcaa | taaaaatttc | ggaaatgcca | gaaatgttat | taagaagtt      960 |
| aaaagcacaa | taaatatttc | gtttcatact | gttgacgaaa | ccataagaaa | tgtatttaaa    1020 |
| gatagtgtac | ctaaaattac | aggattaata | acacaagctg | ggaaatctat | caaaggaata    1080 |
| aataacaaat | ataaaattaa | agagcgtatt | cctaaatata | caaatattat | tttattaact    1140 |
| aatattattt | tattgttacc | accattctta | atattattag | gtatcataat | ttttatgata    1200 |
| tttattctta | tgggatatat | acaaaaaaat | aataatttct | tcataaaatt | atttggtcat    1260 |
| ttcagtgctt | actttggttt | actcactata | attattttat | cctttggaat | actattctta    1320 |
| agtacttcag | tcataggagg | cacatcttgt | attttatcag | aaagaatttt | aaaaaatgaa    1380 |
| ttacgttttg | atatattaaa | taatactctt | atagattatt | gtattaaaaa | tgaaagcgca    1440 |
| ccattaattg | acgatgatat | aacaacaagc | tttgtcgcta | aaattaattc | tttcgataca    1500 |
| ggacatatag | atcataatat | aaacgaatat | gaaaaacatt | ttacaatttt | aaaagaatct    1560 |
| ttttttcata | agtcattaaa | atttatggat | tatatatgga | ttgttataat | gaaacgagaa    1620 |
| aataatacat | ttttaaatag | aataagaact | gaacaagtca | aaaaatcgtt | attaataaca    1680 |

-continued

| | |
|---|---|
| ggtattataa acgaaaatat taaatatgaa aatatggaag ctataggtat cagatcctat | 1740 |
| ttaactacgt tgaacaaaat tatttttcct gaaaataatg gtaaaatatg ttttaatgat | 1800 |
| atcatatgtg aaaaggagaa taatacatat aatattactg agaattcaaa aacaaccgat | 1860 |
| cagaaatata gaaatatacg tgatggaatg atgaacatc ttagaaacga tttggatgct | 1920 |
| ttgttcaact ctttgtttat aaagcacgta ttctaaaaga aaatatattc gatattaacg | 1980 |
| atcttgatag taacgaaaaa aacaaaatag gatggagcga atatacaccc agaaatataa | 2040 |
| atggaacaca aaaaaaatca atcattaata ctttcctagt aaatgttatt gaaagtatta | 2100 |
| acttttcaga aataataaat ttctttgata aaatgagaga tcaatttaat gtacttaaag | 2160 |
| acctaattct attaaaaatt gatacattaa cagaaaatac aaaatgtaat aaattagtaa | 2220 |
| aagaacttat taatgtcaga aaagattatt gtaataacgt cgttttgaat ttatctactt | 2280 |
| tatctgtata tttaattata ttttccatca cttcattttt attatggtat ctatttctat | 2340 |
| tcttgtggtt ctattataat attaaaccat catag | 2375 |

<210> SEQ ID NO 5
<211> LENGTH: 2370
<212> TYPE: DNA
<213> ORGANISM: Plasmodium vivax

<400> SEQUENCE: 5

| | |
|---|---|
| atgagcgacg agtacaacct gagcatcgac ctgaagaaga cggagctgct gaaggagcac | 60 |
| ttgaaagcca ttgccaaagt tatgcacaat gagttcgggt actttttgccc cagtggtgga | 120 |
| gtgaaggtcc cgcaggacca ccccaatgaa ttctcgaaga ccatatggag catcctttac | 180 |
| acgtcctgga ggatggaaga ttttacgagg ctgaatttaa aaagcgtttt gaacatcctc | 240 |
| aagaggaacc cctacgtgat ggggtgtgtg tacttcctca tcatcttcac gtgtgtatat | 300 |
| ctgttaacgt tattcctgta taccaagtgc tttcggaggt tgattaaagc cattcgttgc | 360 |
| aaaacgtgta ggaggaagaa acagaagcga gaacaacagg agagtgaaaa taagagattta | 420 |
| attgaaaatg tgaagaagcg attcttaac atcatgacgt acgtgttttt gagttcgctt | 480 |
| ctgtgtgttc tgattggttt gggcatctgg tatatgattt cttttttcaa aacgaggaat | 540 |
| gggatttata tgaatgtatg cagcgcgtcc acctcgattg agaacttcct caccgaccgc | 600 |
| tgctccgtgc agggcggcga ggtggactcg tcgtgctact ccctggagca catcgtgagc | 660 |
| gacgcggtgt ccatcgtgga gcagtaccaa gacatcaagc tgcagataaa ggcggacctg | 720 |
| ctggtggacag gacagggc ggttccgctc ctcacaggct cctcaccgt gttcgagaac | 780 |
| ctgaagaagc tgcagcagaa cgtggcgcgg aacaaccaca tcctggagga gcagtacttc | 840 |
| cacacgtacc ccgtgctgac gaggctgggc agagcgctcg acgcagtcat ccaggaggga | 900 |
| gaggcgaacc tccagcaggc gacaggcacc ctcgatgaag ccaagcaagc agtcaaagga | 960 |
| gccttcgaag aaatcgacca agttctggga gcaaccttta agaaaatat ggaaaaggta | 1020 |
| aatgacaaaa ttacgctctct caataagtct ataaatagaa taatacacca gtataagata | 1080 |
| aagcaaaatt tgaagaagta cacgatttca atttttgattg tgaagttggt tttgctcatt | 1140 |
| cctccccttc tcattctaat tgggttagtg cttttcatat tctttttggt gaaggggac | 1200 |
| attggaaaca gcagtcattt ttttttggac ctctttggag tgttcagcgc ctactttgga | 1260 |
| tttttgacga tcgtcatttt gctaatcggg atagcaatgc tgagtgcgtc catcttgggg | 1320 |
| gggacgacct gcatcatcgc cgatagggtt ttaaaaaatg agctgaactt tgacgtgctg | 1380 |

```
aatgatacccc tgatcgatta ctgcctgaag aatgaggagt cgccccttct ctcggaggac   1440
atcaccaagg ggcttgtaga caacatgaag tctttggaca ccaccgaaat ggagaggagg   1500
gtgaatgaat acgattccta tttcaacgat atgaagagaa ccttccgcga aaatacaaga   1560
aattttgtca actacatgtg ggtggtcatt accaagccga acaacaacct gtatgtggat   1620
cgaattcggc taaacactct gaaaaagtcc ctcctagcga ccagcatcac tcgggacaat   1680
atcaaatttg gtaaattcaa cctctgggga acagatgaat actttgaaaa tctgaatcgc   1740 cactattta ggggcaccca gtttgccctc tgctttgaaa atgaagaatg cgacagggag   1800
gaggacaagt ttaacatcaa ctttaggtcc tccataaatg accccaagta ccagaggatg   1860
aggaaccacc tcaggaataa tgatcttaga gaggacctag acaacgtggt ggagctattc   1920
atttacaagt ctagagttag gaccgaaaag atattctctg tggacgactt ggatagcagc   1980
atgacggaca aaataggtg gagtgagtac acgccgagga ttaacaaaag ggaggggggg   2040
aaagaacaaa ccttcatttt gaggaagtac ctcgtggagg acattgaaaa tttgaacttc   2100
aaagacgtgg ttagcttctt cgagaaaatt aaacagaaat tcaacaccct cagagacacg   2160
atcattacga aggtgcagat gctcgtgaag aacaccaact gcagcagact cgttggcgag   2220
atgcacaatt tgaaacacat ctactgcgac cgagtcgtgc tgaacatgac catcctctcc   2280
gtcgcgctcg tctccttctc catcatttcg ttcttcctct ggtactgctt tttgttcttt   2340
tggctgtact accagatgaa gatgatgtga                                    2370

<210> SEQ ID NO 6
<211> LENGTH: 789
<212> TYPE: PRT
<213> ORGANISM: Plasmodium vivax

<400> SEQUENCE: 6

Met Ser Asp Glu Tyr Asn Leu Ser Ile Asp Leu Lys Lys Thr Glu Leu
1               5                   10                  15

Leu Lys Glu His Leu Lys Ala Ile Ala Lys Val Met His Asn Glu Phe
                20                  25                  30

Gly Tyr Phe Cys Pro Ser Gly Gly Val Lys Val Pro Gln Asp His Pro
            35                  40                  45

Asn Glu Phe Ser Lys Thr Ile Trp Ser Ile Leu Tyr Thr Ser Trp Arg
        50                  55                  60

Met Glu Asp Phe Thr Arg Leu Asn Leu Lys Ser Val Leu Asn Ile Leu
65                  70                  75                  80

Lys Arg Asn Pro Tyr Val Met Gly Cys Val Tyr Phe Leu Ile Ile Phe
                85                  90                  95

Thr Cys Val Tyr Leu Leu Thr Leu Phe Leu Tyr Thr Lys Cys Phe Arg
                100                 105                 110

Arg Leu Ile Lys Ala Ile Arg Cys Lys Thr Cys Arg Arg Lys Lys Gln
            115                 120                 125

Lys Arg Glu Gln Gln Glu Ser Glu Asn Lys Asp Leu Ile Glu Asn Val
        130                 135                 140

Lys Lys Arg Phe Phe Asn Ile Met Thr Tyr Val Phe Leu Ser Ser Leu
145                 150                 155                 160

Leu Cys Val Leu Ile Gly Leu Gly Ile Trp Tyr Met Ile Ser Phe Phe
                165                 170                 175

Lys Thr Arg Asn Gly Ile Tyr Met Asn Val Cys Ser Ala Ser Thr Ser
                180                 185                 190

Ile Glu Asn Phe Leu Thr Asp Arg Cys Ser Val Gln Gly Gly Glu Val
```

-continued

```
                195                 200                 205
Asp Ser Ser Cys Tyr Ser Leu Glu His Ile Val Ser Asp Ala Val Ser
210                 215                 220
Ile Val Glu Gln Tyr Gln Asp Ile Lys Leu Gln Ile Lys Ala Asp Leu
225                 230                 235                 240
Leu Val Asp Glu Asp Arg Ala Val Pro Leu Thr Gly Phe Leu Thr
                245                 250                 255
Val Phe Glu Asn Leu Lys Lys Leu Gln Gln Asn Val Ala Arg Asn Asn
                260                 265                 270
His Ile Leu Glu Glu Gln Tyr Phe His Thr Tyr Pro Val Leu Thr Arg
                275                 280                 285
Leu Gly Arg Ala Leu Asp Ala Val Ile Gln Glu Gly Glu Ala Asn Leu
                290                 295                 300
Gln Gln Ala Thr Gly Thr Leu Asp Glu Ala Lys Gln Ala Val Lys Gly
305                 310                 315                 320
Ala Phe Glu Glu Ile Asp Gln Val Leu Gly Ala Thr Phe Lys Glu Asn
                325                 330                 335
Met Glu Lys Val Asn Asp Lys Ile Thr Leu Phe Asn Lys Ser Ile Asn
                340                 345                 350
Arg Ile Ile His Gln Tyr Lys Ile Lys Gln Asn Leu Lys Lys Tyr Thr
                355                 360                 365
Ile Ser Ile Leu Ile Val Lys Leu Val Leu Leu Ile Pro Pro Leu Leu
370                 375                 380
Ile Leu Ile Gly Leu Val Leu Phe Ile Phe Phe Leu Val Lys Gly Asp
385                 390                 395                 400
Ile Gly Asn Ser Ser His Phe Phe Leu Asp Leu Phe Gly Val Phe Ser
                405                 410                 415
Ala Tyr Phe Gly Phe Leu Thr Ile Val Ile Leu Leu Ile Gly Ile Ala
                420                 425                 430
Met Leu Ser Ala Ser Ile Leu Gly Gly Thr Thr Cys Ile Ile Ala Asp
                435                 440                 445
Arg Val Leu Lys Asn Glu Leu Asn Phe Asp Val Leu Asn Asp Thr Leu
450                 455                 460
Ile Asp Tyr Cys Leu Lys Asn Glu Glu Ser Pro Leu Leu Ser Glu Asp
465                 470                 475                 480
Ile Thr Lys Gly Leu Val Asp Asn Met Lys Ser Leu Asp Thr Thr Glu
                485                 490                 495
Met Glu Arg Arg Val Asn Glu Tyr Asp Ser Tyr Phe Asn Asp Met Lys
                500                 505                 510
Arg Thr Phe Arg Glu Asn Thr Arg Asn Phe Val Asn Tyr Met Trp Val
                515                 520                 525
Val Ile Thr Lys Pro Asn Asn Asn Leu Tyr Val Asp Arg Ile Arg Leu
530                 535                 540
Asn Thr Leu Lys Lys Ser Leu Leu Ala Thr Ser Ile Thr Arg Asp Asn
545                 550                 555                 560
Ile Lys Phe Gly Lys Phe Asn Leu Trp Gly Thr Asp Glu Tyr Phe Glu
                565                 570                 575
Asn Leu Asn Arg His Tyr Phe Arg Gly Thr Gln Phe Ala Leu Cys Phe
                580                 585                 590
Glu Asn Glu Glu Cys Asp Arg Glu Glu Asp Lys Phe Asn Ile Asn Phe
                595                 600                 605
Arg Ser Ser Ile Asn Asp Pro Lys Tyr Gln Arg Met Arg Asn His Leu
                610                 615                 620
```

```
Arg Asn Asn Asp Leu Arg Glu Asp Leu Asp Asn Val Val Glu Leu Phe
625                 630                 635                 640

Ile Tyr Lys Ser Arg Val Arg Thr Glu Lys Ile Phe Ser Val Asp Asp
            645                 650                 655

Leu Asp Ser Ser Met Thr Asp Lys Ile Gly Trp Ser Glu Tyr Thr Pro
            660                 665                 670

Arg Ile Asn Lys Arg Glu Gly Gly Lys Glu Gln Thr Phe Ile Leu Arg
            675                 680                 685

Lys Tyr Leu Val Glu Asp Ile Glu Asn Leu Asn Phe Lys Asp Val Val
        690                 695                 700

Ser Phe Phe Glu Lys Ile Lys Gln Lys Phe Asn Thr Leu Arg Asp Thr
705                 710                 715                 720

Ile Ile Thr Lys Val Gln Met Leu Val Lys Asn Thr Asn Cys Ser Arg
                725                 730                 735

Leu Val Gly Glu Met His Asn Leu Lys His Ile Tyr Cys Asp Arg Val
            740                 745                 750

Val Leu Asn Met Thr Ile Leu Ser Val Ala Leu Val Ser Phe Ser Ile
            755                 760                 765

Ile Ser Phe Phe Leu Trp Tyr Cys Phe Leu Phe Trp Leu Tyr Tyr
        770                 775                 780

Gln Met Lys Met Met
785

<210> SEQ ID NO 7
<211> LENGTH: 413
<212> TYPE: PRT
<213> ORGANISM: Plasmodium falciparum

<400> SEQUENCE: 7

Met Asn Leu Leu Val Phe Phe Cys Phe Phe Leu Leu Ser Cys Ile Val
1               5                   10                  15

His Leu Ser Arg Cys Ser Asp Asn Asn Ser Tyr Ser Phe Glu Ile Val
            20                  25                  30

Asn Arg Ser Thr Trp Leu Asn Ile Ala Glu Arg Ile Phe Lys Gly Asn
        35                  40                  45

Ala Pro Phe Asn Phe Thr Ile Ile Pro Tyr Asn Tyr Val Asn Asn Ser
    50                  55                  60

Thr Glu Glu Asn Asn Asn Lys Asp Ser Val Leu Leu Ile Ser Lys Asn
65                  70                  75                  80

Leu Lys Asn Ser Ser Asn Pro Val Asp Glu Asn His Ile Ile Asp
                85                  90                  95

Ser Thr Lys Lys Asn Thr Ser Asn Asn Asn Asn Asn Ser Asn Ile
            100                 105                 110

Val Gly Ile Tyr Glu Ser Gln Val His Glu Lys Ile Lys Glu Asp
        115                 120                 125

Asn Thr Arg Gln Asp Asn Ile Asn Lys Lys Glu Asn Glu Ile Ile Asn
    130                 135                 140

Asn Asn His Gln Ile Pro Val Ser Asn Ile Phe Ser Glu Asn Ile Asp
145                 150                 155                 160

Asn Asn Lys Asn Tyr Ile Glu Ser Asn Tyr Lys Ser Thr Tyr Asn Asn
                165                 170                 175

Asn Pro Glu Leu Ile His Ser Thr Asp Phe Ile Gly Ser Asn Asn Asn
            180                 185                 190

His Thr Phe Asn Phe Leu Ser Arg Tyr Asn Asn Ser Val Leu Asn Asn
```

```
            195                 200                 205
Met Gln Gly Asn Thr Lys Val Pro Gly Asn Val Pro Glu Leu Lys Ala
            210                 215                 220

Arg Ile Phe Ser Glu Glu Asn Thr Glu Val Glu Ser Ala Glu Asn
225                 230                 235                 240

Asn His Thr Asn Ser Leu Asn Pro Asn Glu Ser Cys Asp Gln Ile Ile
                    245                 250                 255

Lys Leu Gly Asp Ile Ile Asn Ser Val Asn Glu Lys Ile Ile Ser Ile
            260                 265                 270

Asn Ser Thr Val Asn Asn Val Leu Cys Ile Asn Leu Asp Ser Val Asn
                275                 280                 285

Gly Asn Gly Phe Val Trp Thr Leu Leu Gly Val His Lys Lys Lys Pro
            290                 295                 300

Leu Ile Asp Pro Ser Asn Phe Pro Thr Lys Arg Val Thr Gln Ser Tyr
305                 310                 315                 320

Val Ser Pro Asp Ile Ser Val Thr Asn Pro Val Pro Ile Pro Lys Asn
                325                 330                 335

Ser Asn Thr Asn Lys Asp Asp Ser Ile Asn Asn Lys Gln Asp Gly Ser
                340                 345                 350

Gln Asn Asn Thr Thr Thr Asn His Phe Pro Lys Pro Arg Glu Gln Leu
            355                 360                 365

Val Gly Gly Ser Ser Met Leu Ile Ser Lys Ile Lys Pro His Lys Pro
            370                 375                 380

Gly Lys Tyr Phe Ile Val Tyr Ser Tyr Arg Pro Phe Asp Pro Thr
385                 390                 395                 400

Arg Asp Thr Asn Thr Arg Ile Val Glu Leu Asn Val Gln
                    405                 410

<210> SEQ ID NO 8
<211> LENGTH: 397
<212> TYPE: PRT
<213> ORGANISM: Plasmodium falciparum

<400> SEQUENCE: 8

Met Met Arg Lys Leu Ala Ile Leu Ser Val Ser Ser Phe Leu Phe Val
1               5                   10                  15

Glu Ala Leu Phe Gln Glu Tyr Gln Cys Tyr Gly Ser Ser Ser Asn Thr
                20                  25                  30

Arg Val Leu Asn Glu Leu Asn Tyr Asp Asn Ala Gly Thr Asn Leu Tyr
            35                  40                  45

Asn Glu Leu Glu Met Asn Tyr Tyr Gly Lys Gln Glu Asn Trp Tyr Ser
        50                  55                  60

Leu Lys Lys Asn Ser Arg Ser Leu Gly Glu Asn Asp Asp Gly Asn Asn
65                  70                  75                  80

Glu Asp Asn Glu Lys Leu Arg Lys Pro Lys His Lys Lys Leu Lys Gln
                85                  90                  95

Pro Ala Asp Gly Asn Pro Asp Pro Asn Ala Asn Pro Asn Val Asp Pro
                100                 105                 110

Asn Ala Asn Pro Asn Val Asp Pro Asn Ala Asn Pro Asn Val Asp Pro
            115                 120                 125

Asn Ala Asn Pro Asn Ala Asn Pro Asn Ala Asn Pro Asn Ala Asn Pro
            130                 135                 140

Asn Ala Asn Pro Asn Ala Asn Pro Asn Ala Asn Pro Asn Ala Asn Pro
145                 150                 155                 160
```

Asn Ala Asn Pro Asn Ala Asn Pro Asn Ala Asn Pro Asn Ala Asn Pro
            165                 170                 175

Asn Ala Asn Pro Asn Ala Asn Pro Asn Ala Asn Pro Asn Ala Asn Pro
        180                 185                 190

Asn Ala Asn Pro Asn Val Asp Pro Asn Ala Asn Pro Asn Ala Asn Pro
    195                 200                 205

Asn Ala Asn Pro Asn Ala Asn Pro Asn Ala Asn Pro Asn Ala Asn Pro
210                 215                 220

Asn Ala Asn Pro Asn Ala Asn Pro Asn Ala Asn Pro Asn Ala Asn Pro
225                 230                 235                 240

Asn Ala Asn Pro Asn Ala Asn Pro Asn Ala Asn Pro Asn Ala Asn Pro
            245                 250                 255

Asn Ala Asn Pro Asn Ala Asn Pro Asn Ala Asn Pro Asn Ala Asn Pro
        260                 265                 270

Asn Lys Asn Asn Gln Gly Asn Gly Gln Gly His Asn Met Pro Asn Asp
    275                 280                 285

Pro Asn Arg Asn Val Asp Glu Asn Ala Asn Ala Asn Ser Ala Val Lys
290                 295                 300

Asn Asn Asn Asn Glu Glu Pro Ser Asp Lys His Ile Lys Glu Tyr Leu
305                 310                 315                 320

Asn Lys Ile Gln Asn Ser Leu Ser Thr Glu Trp Ser Pro Cys Ser Val
            325                 330                 335

Thr Cys Gly Asn Gly Ile Gln Val Arg Ile Lys Pro Gly Ser Ala Asn
        340                 345                 350

Lys Pro Lys Asp Glu Leu Asp Tyr Ala Asn Asp Ile Glu Lys Lys Ile
    355                 360                 365

Cys Lys Met Glu Lys Cys Ser Ser Val Phe Asn Val Val Asn Ser Ser
370                 375                 380

Ile Gly Leu Ile Met Val Leu Ser Phe Leu Phe Leu Asn
385                 390                 395

<210> SEQ ID NO 9
<211> LENGTH: 229
<212> TYPE: PRT
<213> ORGANISM: Plasmodium falciparum

<400> SEQUENCE: 9

Met Lys Val Ser Lys Leu Val Leu Phe Ala His Ile Phe Phe Ile Ile
1               5                   10                  15

Asn Ile Leu Cys Gln Tyr Ile Cys Leu Asn Ala Ser Lys Val Asn Lys
            20                  25                  30

Lys Gly Lys Ile Ala Glu Glu Lys Arg Lys Asn Ile Lys Asn Ile
        35                  40                  45

Asp Lys Ala Ile Glu Glu His Asn Lys Arg Lys Lys Leu Ile Tyr Tyr
    50                  55                  60

Ser Leu Ile Ala Ser Gly Ala Ile Ala Ser Val Ala Ala Ile Leu Gly
65                  70                  75                  80

Leu Gly Tyr Tyr Gly Tyr Lys Lys Ser Arg Glu Asp Asp Leu Tyr Tyr
                85                  90                  95

Asn Lys Tyr Leu Glu Tyr Arg Asn Gly Glu Tyr Asn Ile Lys Tyr Gln
            100                 105                 110

Asp Gly Ala Ile Ala Ser Thr Ser Glu Phe Tyr Ile Glu Pro Glu Gly
        115                 120                 125

Ile Asn Lys Ile Asn Leu Asn Lys Pro Ile Ile Glu Asn Lys Asn Asn
    130                 135                 140

```
Val Asp Val Ser Ile Lys Arg Tyr Asn Asn Phe Val Asp Ile Ala Arg
145                 150                 155                 160

Leu Ser Ile Gln Lys His Phe Glu His Leu Ser Asn Asp Gln Lys Asp
                165             170                 175

Ser His Val Asn Asn Met Glu Tyr Met Gln Lys Phe Val Gln Gly Leu
            180             185                 190

Gln Glu Asn Arg Asn Ile Ser Leu Ser Lys Tyr Gln Glu Asn Lys Ala
        195             200             205

Val Met Asp Leu Lys Tyr His Leu Gln Lys Val Tyr Ala Asn Tyr Leu
    210             215             220

Ser Gln Glu Glu Asn
225
```